(12) United States Patent
Cloutier et al.

(10) Patent No.: US 8,317,869 B2
(45) Date of Patent: Nov. 27, 2012

(54) FEMORAL COMPONENT OF KNEE PROSTHESIS, THE FEMORAL COMPONENT HAVING ANTERIOR/POSTERIOR CLAW(S) FOR DIGGING INTO BONE AND/OR A RAISED RIB WITH A BULBOUS TERMINUS

(75) Inventors: Raymond J. Cloutier, Alachua, FL (US); James Madden, High Springs, FL (US); Nicolas Hohl, Niederbronn (FR)

(73) Assignee: Exactech, Inc., Gainesville, FL (US)

( * ) Notice: Subject to any disclaimer, the term of this patent is extended or adjusted under 35 U.S.C. 154(b) by 164 days.

(21) Appl. No.: 12/367,268

(22) Filed: Feb. 6, 2009

(65) Prior Publication Data

US 2009/0198340 A1  Aug. 6, 2009

Related U.S. Application Data

(60) Provisional application No. 61/026,616, filed on Feb. 6, 2008, provisional application No. 61/026,636, filed on Feb. 6, 2008.

(51) Int. Cl.
*A61F 2/38* (2006.01)
(52) U.S. Cl. .................... 623/20.3; 623/20.31
(58) Field of Classification Search ........ 623/20.13–20.2, 623/20.11, 20.3, 20.31, 19.11
See application file for complete search history.

(56) References Cited

U.S. PATENT DOCUMENTS

| | | | |
|---|---|---|---|
| 3,837,009 A | 9/1974 | Walker | |
| 5,171,244 A | 12/1992 | Caspari et al. | |
| 5,228,459 A | 7/1993 | Caspari et al. | |
| 5,263,498 A | 11/1993 | Caspari et al. | |
| 5,304,181 A | 4/1994 | Caspari et al. | |
| 5,395,376 A | 3/1995 | Caspari et al. | |
| 5,454,331 A | 10/1995 | Green | |
| 5,941,881 A | 8/1999 | Barnes | |
| 6,165,221 A * | 12/2000 | Schmotzer | 623/20.11 |
| 6,494,914 B2 | 12/2002 | Brown et al. | |
| 6,610,067 B2 | 8/2003 | Tallarida et al. | |

(Continued)

FOREIGN PATENT DOCUMENTS
WO  2009/100369 A1  8/2009

OTHER PUBLICATIONS

Moment of Inertia Tables, Efunda Engineering Principles.*

(Continued)

*Primary Examiner* — Bruce E Snow
*Assistant Examiner* — Brian Dukert
(74) *Attorney, Agent, or Firm* — Greenberg, Traurig, LLP

(57) ABSTRACT

A femoral component of a knee prosthesis, wherein the femoral component includes a sharp radius at each end (e.g., the anterior end and the posterior end) of the femoral component is disclosed herein. The sharp radius at each end may form a "claw" at each end. Each of these claws may "dig" through the patient's cartilage into the bone (or may "dig" directly into bone if there is no intervening cartilage). One benefit provided by a claw may be facilitating a smooth transition of cartilage/poly bearing to femoral implant/poly bearing (e.g., during knee extension). A femoral component of a knee prosthesis, wherein the femoral component includes a raised rib having a bulbous terminus at a free edge is disclosed herein. This raised rib having a bulbous terminus at a free edge may, for example, simultaneously create sufficient implant strength and adequate cement fixation while minimizing the component's thickness.

8 Claims, 21 Drawing Sheets

U.S. PATENT DOCUMENTS

| | | | |
|---|---|---|---|
| 6,679,917 | B2 | 1/2004 | Ek |
| 7,029,479 | B2 | 4/2006 | Tallarida et al. |
| 2004/0083005 | A1 | 4/2004 | Jacobsson et al. |
| 2006/0111787 | A1* | 5/2006 | Bailie et al. ............... 623/19.13 |
| 2006/0167460 | A1* | 7/2006 | Pinczewski et al. ............. 606/88 |
| 2006/0235537 | A1* | 10/2006 | Kuczynski et al. ........... 623/20.3 |
| 2007/0233266 | A1 | 10/2007 | Williams, III et al. |
| 2007/0299530 | A1* | 12/2007 | Rhodes et al. ............. 623/20.32 |

OTHER PUBLICATIONS

Arthosurface—AKR Knee—Partial Knee Resurfacing (4 pgs) © 2009 Arthosurface, All Rights Reserved.
Arthosurface—Knee—Product Overview (2 pgs) © 2009 Arthosurface, All Rights Reserved.
Arthosurface—Knee—Existing Treatments (4 pgs) © 2009 Arthosurface, All Rights Reserved.
Arthosurface—Knee—Cartilage Damage (4 pgs) © 2009 Arthosurface, All Rights Reserved.
Arthosurface—Knee—Patello-Femoral (2 pgs) ©2009 Arthosurface, All Rights Reserved.
Arthosurface—Knee—Patello-Femoral—Product Overview (2 pgs) © 2009 Arthosurface, All Rights Reserved.
Arthosurface—Knee—Patello-Femoral—Joint Anatomy (2 pgs) © 2009 Arthosurface, All Rights Reserved.
Arthosurface—Knee—Patello-Femoral—Cartilage Damage (2 pgs) © 2009 Arthosurface, All Rights Reserved.
Arthosurface—Knee—Patello-Femoral—Existing Treatments (3 pgs) © 2009 Arthosurface, All Rights Reserved.
Arthosurface—Scientific Collection: Knee—Patello-Femoral HemiCAP® Resurfacing: Publications (6 pgs) © 2009 Arthosurface, All Rights Reserved.
Arthosurface—Knee—Condyle (2 pgs) © 2009 Arthosurface, All Rights Reserved.
Arthosurface—Knee—Condyle—Product Overview (2 pgs) © 2009 Arthosurface, All Rights Reserved.
Arthosurface—Knee—Condyle—Joint Anatomy (2 pgs) © 2009 Arthosurface, All Rights Reserved.
Arthosurface—Knee—Condyle—Existing Treatments (4 pgs) © 2009 Arthosurface, All Rights Reserved.
Arthosurface—Knee—Condyle—Cartilage Damage (4 pgs) © 2009 Arthosurface, All Rights Reserved.
Arthosurface—Knee—Condyle—Scientific Collection: Knee—Focal Femoral Condyle HemiCAP Resurfacing (28 pgs) © 2009 Arthosurface, All Rights Reserved.
Johnson & Johnson Gateway®: Preservation—Minimally Invasive Unicondylar Knee System (2 pgs) © 2009 Johnson & Johnson Gateway, LLC 2000-2009.
Johnson & Johnson Gateway®: Total and Uni-Compartmental Knee Prosthesis (2 pgs) © 2009 Johnson & Johnson Gateway, LLC 2000-2009.
Johnson & Johnson Gateway®: Preservation—Minimally Invasive Unicondylar Knee System Overview (3 pgs) © 2009 Johnson & Johnson Gateway, LLC 2000-2009.
BioMet Preservation (1 pg).
Mako Surgical Corp.—Implants: Restoris® Unicompartmental Knee System (2 pgs) © MAKO Surgical Corp. 2007-2008.
Stulberg, S. David et al., Johnson & Johnson—Orthopedics: Principles and Techniques of Unicompartmental Knee Arthoplasty: The MICROLOC™ Unicompartmental Knee System with SPECIALIST™ Instrumentation (10 pgs).
International Search Report from PCT/US2009/03347 dated Mar. 25, 2009.

* cited by examiner

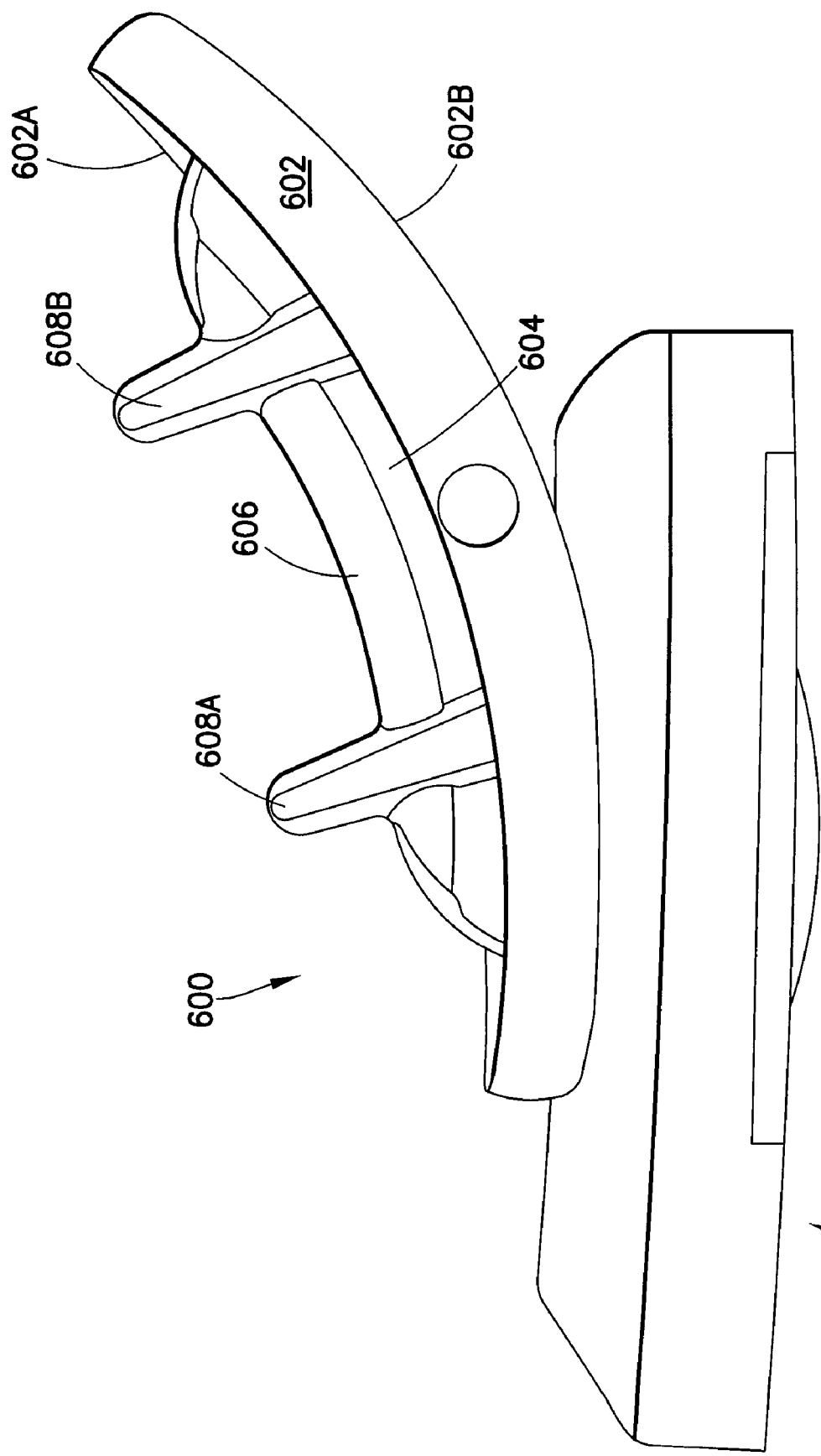

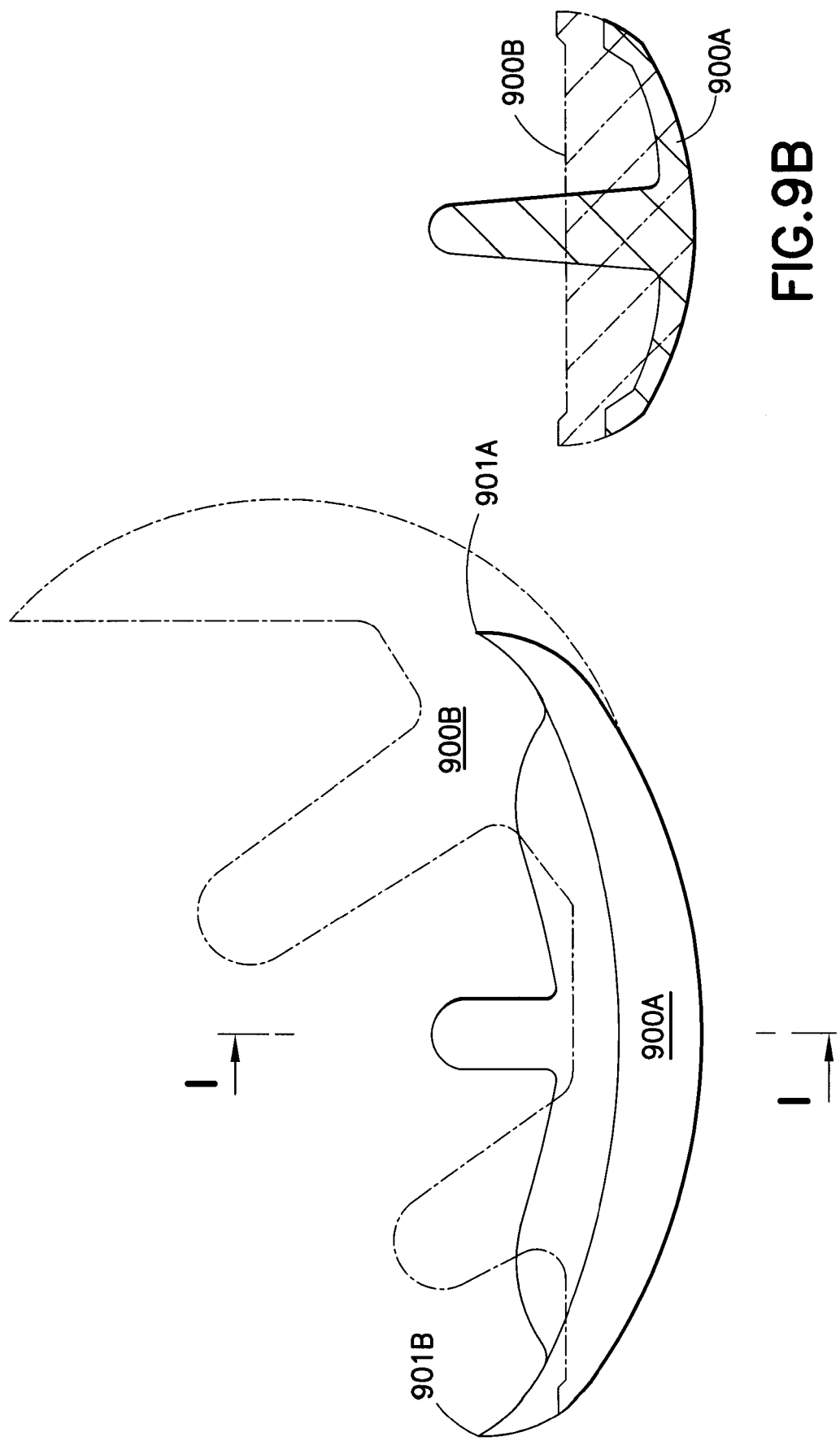

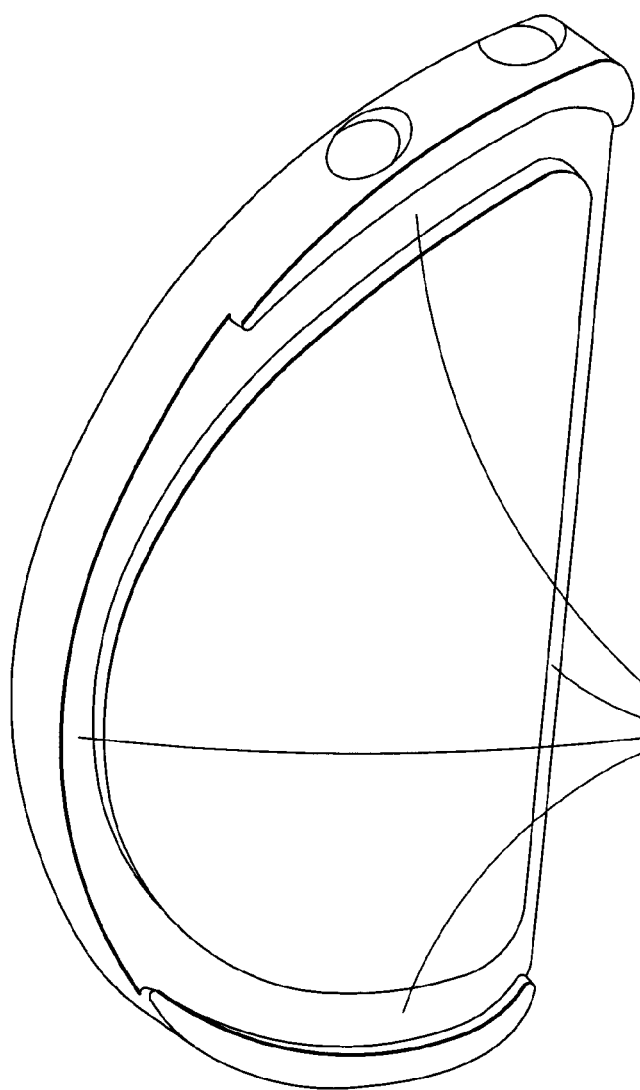
FIG.24 DOVETAIL GROOVE
FIG.26

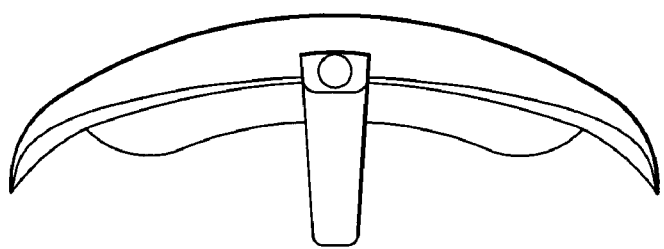
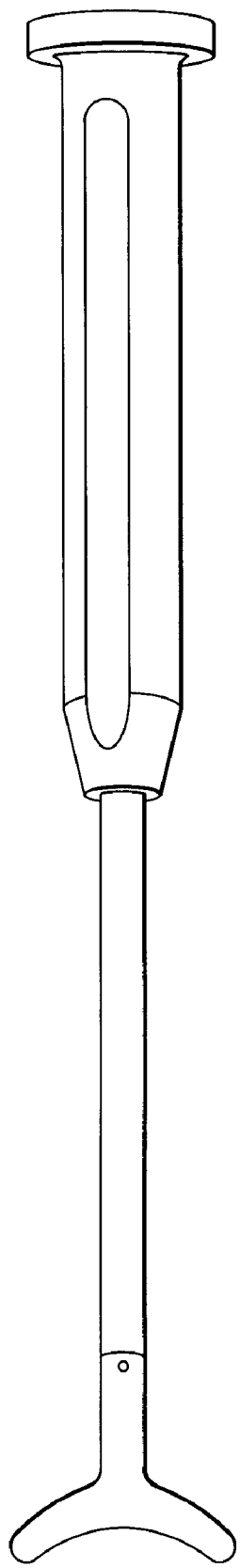
FIG.25A
FIG.25B

FEMORAL COMPONENT OF KNEE PROSTHESIS, THE FEMORAL COMPONENT HAVING ANTERIOR/POSTERIOR CLAW(S) FOR DIGGING INTO BONE AND/OR A RAISED RIB WITH A BULBOUS TERMINUS

RELATED APPLICATIONS

This application claims the benefit of U.S. Provisional Application Ser. No. 61/026,616, filed Feb. 6, 2008. This application also claims the benefit of U.S. Provisional Application Ser. No. 61/026,636, filed Feb. 6, 2008. Each of the aforementioned applications is incorporated herein by reference in its entirety.

FIELD OF THE INVENTION

One embodiment of the present invention provides a femoral component of a knee prosthesis, wherein the femoral component includes a sharp radius at each end (e.g., the anterior end and the posterior end) of the femoral component. The sharp radius at each end may form a "claw" at each end. Each of these claws may "dig" through the patient's cartilage into the bone (or may "dig" directly into bone if there is no intervening cartilage). Enhanced fixation may be achieved with the claws "digging" and fixing into the bone as well as the claws providing additional cement pressurization (e.g., with the claws in the bone, cement is less likely to escape by the anterior and posterior ends). Further, one benefit provided by a claw may be facilitating a smooth transition of cartilage/poly bearing to femoral implant/poly bearing (e.g., during knee extension).

Another embodiment of the present invention provides a femoral component of a knee prosthesis, wherein the femoral component includes a raised rib having a bulbous terminus at a free edge. This raised rib having a bulbous terminus at a free edge may, for example, simultaneously create sufficient implant strength and adequate cement fixation while minimizing the component's thickness (e.g., in order to minimize the amount of bone that must be removed to fit a unicompartmental femoral component that is used for patients who have early stage arthritis). Accomplishing all three attributes (i.e. strength, cement fixation and minimal size) simultaneously has typically been difficult because these are competing objectives.

Another embodiment of the present invention relates to an implant system associated with knee surgery. Another embodiment of the present invention relates to a surgical technique associated with knee surgery. Another embodiment of the present invention relates to instruments associated with knee surgery.

In one example, the present invention provides an arthroscopically assisted procedure to serve as a minimally invasive operation to improve the quality of life for patients who have knee pain secondary to single compartment disease but are not candidates for a total knee replacement. Various aspects of the invention provide implants, instruments, trials and surgical techniques that allow for arthroscopic preparation of the joint, at least in part, prior to implantation.

In another example, the present invention provides femoral and tibial components that allow for resurfacing of the bone with minimal bone removal so that if degeneration progresses, revision surgery can be accomplished by making standard bone cuts to implant a primary tricompartmental knee.

For the purposes of describing and claiming the present invention, the term "claw" is intended to include a hook, a sharp curved surface, and the like.

Further, for the purposes of describing and claiming the present invention, the term "bulbous" is intended to refer to being enlarged, swollen, bulging or the like (in various examples, the "bulbous" terminus of the present invention may be rounded in cross section, oval in cross section, square in cross section, rectangular in cross section or triangular in cross-section).

BACKGROUND OF THE INVENTION

Conventional techniques for performing total knee replacement and/or uni-compartmental knee replacement exist.

In addition, conventional implants related to performing total knee replacement and/or uni-compartmental knee replacement exist.

BRIEF DESCRIPTION OF THE DRAWINGS

FIG. 6 shows a side view of a femoral component according to another embodiment of the present invention as interfacing with a corresponding tibial component.

FIG. 8B shows −30 degrees of motion; and FIG. 8C shows 30 degrees of motion).

FIGS. 9A and 9B show other views of a femoral component according to an embodiment of the present invention (FIG. 9A is a side view and FIG. 9B is cross section taken through line I-I of FIG. 9A; in addition, it is noted that these FIGS. 9A and 9B show a femoral component with anterior and posterior "claws" according to an embodiment of the present invention (drawn in these Figs. with a darker line) overlaid with a conventional unicompartmental femoral component without such "claws" (drawn in these Figs. with a lighter line)).

FIGS. 11-28 show various instrumentation (and applications thereof) in connection with an example surgical technique according to an embodiment of the present invention.

Figure 1A:
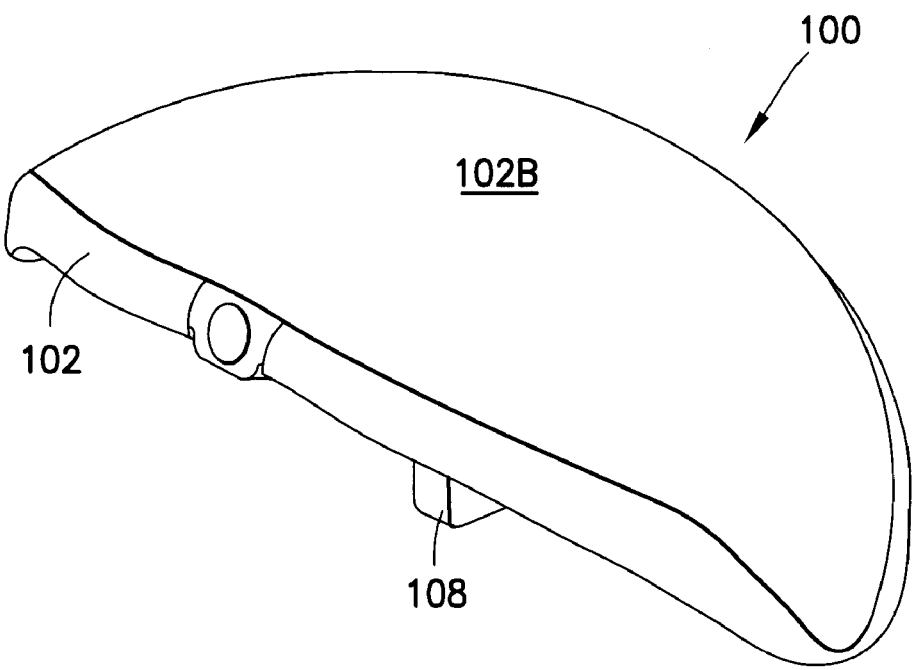
FIGS. 1A and 1B show, respectively, a top and side view of a femoral component portion of a knee prosthesis according to an embodiment of the present invention.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, any figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As mentioned above, one embodiment of the present invention provides a femoral component of a knee prosthesis, wherein the femoral component includes a sharp radius (e.g., having a knife edge or the like) at each end (e.g., the anterior end and the posterior end) of the femoral component. The sharp radius at each end may form a "claw" at each end. Each of these claws may "dig" through the patient's cartilage into the bone (or may "dig" directly into bone if there is no intervening cartilage).

In one example, such claws may assist implant-cartilage transition. In one specific example, such claws may assist implant-cartilage transition during activities requiring flexion angles greater than about 58 degrees (e.g. stair climbing or rising from a chair). In another example, such claws may assist femoral implant fixation to the femoral bone. Of note, a poor transition could lead to early component failure and/or articular cartilage damage.

Of further note, before the addition of the claws, there was a potential for the edge (e.g., anterior and/or posterior edge) of the femoral implant to be on the same level as the articular cartilage, which would typically lead to edge loading and potential implant loosening. The use of the claws as provided herein, however, may reduce or eliminate the potential for the edge (e.g., anterior and/or posterior edge) of the femoral implant to be on the same level as the articular cartilage—the sharp radius nearly eliminates this situation as the articular cartilage will, in various embodiments of the present invention be adjacent to solid metal instead of a metal rim. Each claw may also produce a small gap (e.g., a triangular gap) between the implant and the cartilage (fibrocartilage is anticipated to grow in that region, as fibrocartilage is known to grow into small defects where bone is exposed).

Further, as mentioned above, another embodiment of the present invention provides a femoral component of a knee prosthesis, wherein the femoral component includes a raised rib having a bulbous terminus at a free edge. This raised rib having a bulbous terminus at a free edge may, for example, simultaneously create sufficient implant strength and adequate cement fixation while minimizing the component's thickness.

Of note, the bulbous terminus crossection of the rib may interlock with the bone cement to provide significantly greater implant-to-cement fixation than a conventional flat-sided rib (that is, this femoral rib design may confer sufficient strength and stiffness to the thin femoral implant while providing a means for interlocking the cement for improved fixation). In one example, the femoral component thickness may be less than about 2 mm and the rib height may be less than about 6 mm. This example configuration may enable the surgeon to conserve bone while providing the patient with an implant in which only the region of the knee affected e.g., by arthritis, needs to be resurfaced.

Of further note, it is believed that conventional femoral components typically have flat sided geometries (as opposed, for example, to the above-mentioned rib (e.g., central rib) that has a bulbous terminus crossection). A shortcoming of a flat-sided geometry is that greater height is typically required to confer an equivalent stiffness to that produced by the crosssection of the bulbous terminus. In addition, bone cement (which typically behaves more like a grout than an adhesive), typically depends on undercut structures to transfer load. Therefore, flat-sided fins typically provide little to no resistance to tipping forces (e.g., A/P tipping forces)—therefore putting these conventional implants at greater risk of loosening.

Figure 1B:
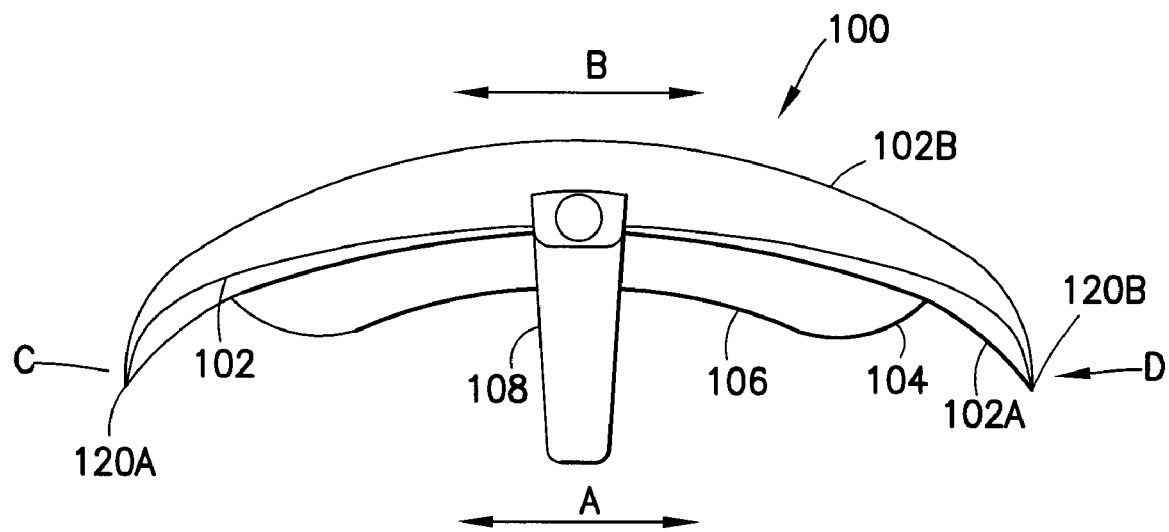
Figure 2A:
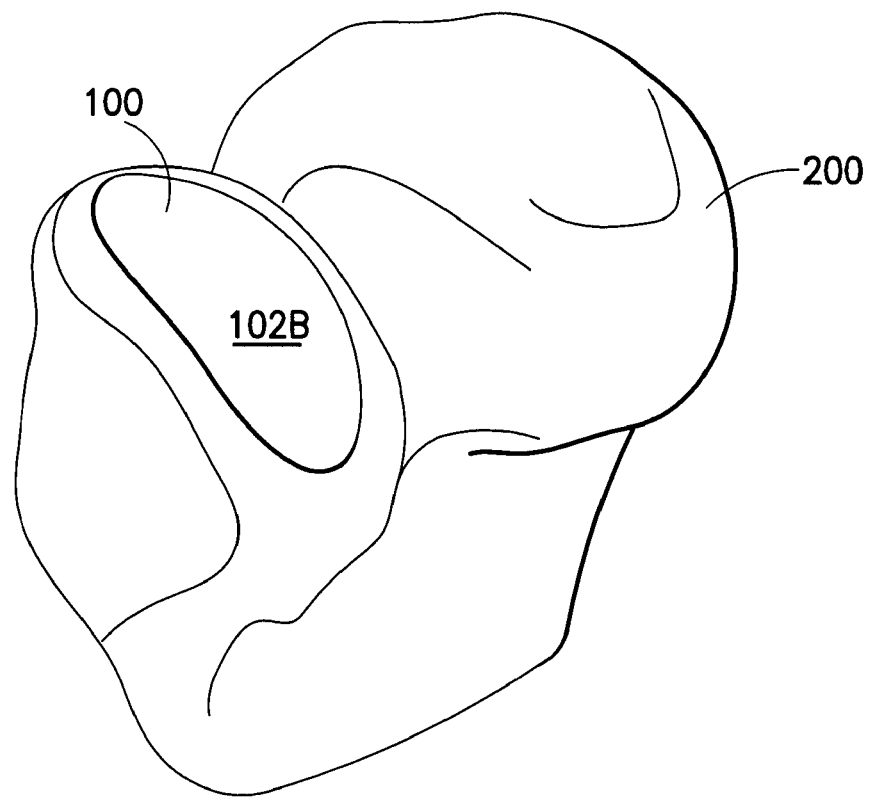
FIGS. 2A and 2B show, respectively, a side and top view of the femoral component of FIGS. 1A and 1B as applied to a femur bone.
Figure 2B:
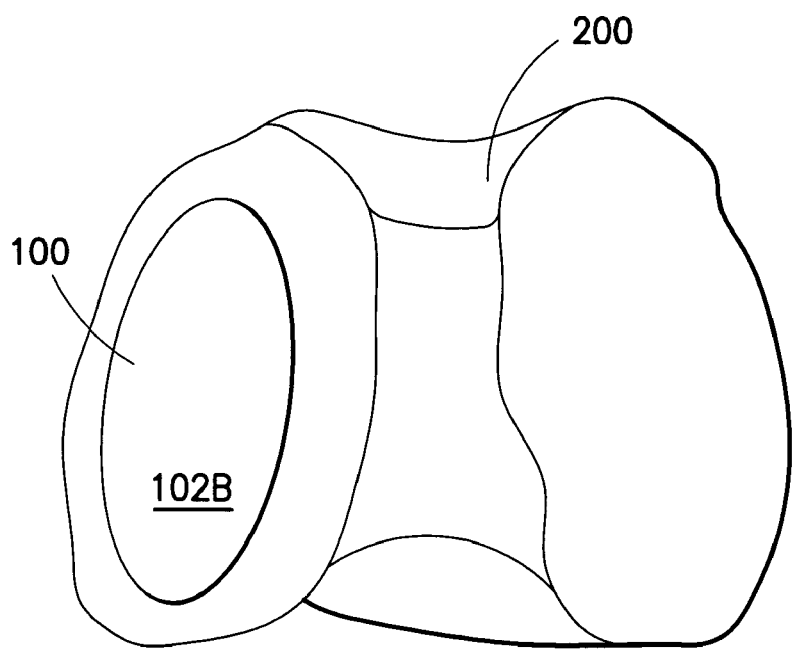

Referring now to FIGS. 1A and 1B a top view (FIG. 1A) and side view (FIG. 1B) of a femoral component 100 portion of a knee prosthesis according to an embodiment of the present invention is shown. Further, FIGS. 2A and 2B show, respectively, a side and top view of the femoral component 100 of FIGS. 1A and 1B as applied to a femur bone 200.

Figure 4:
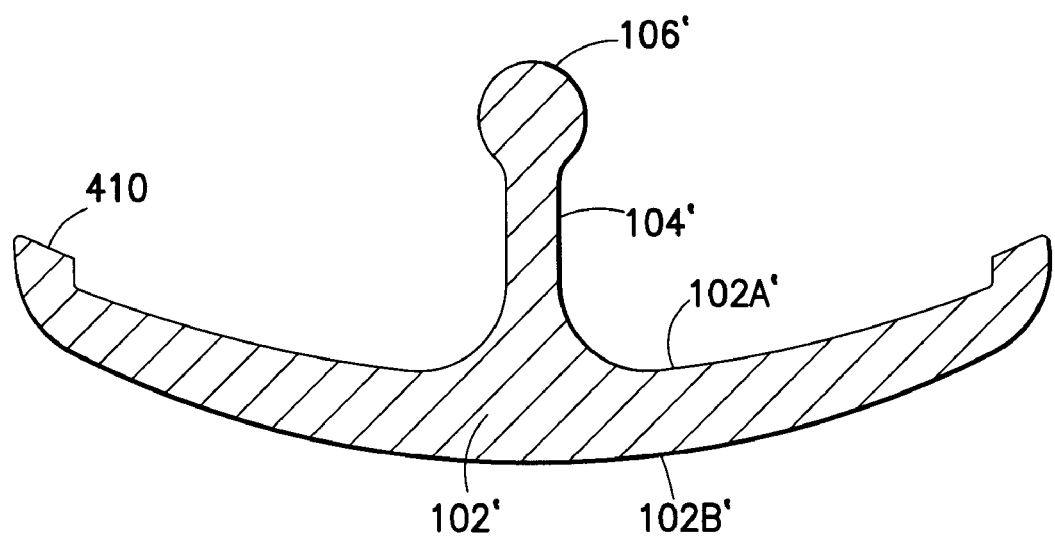
FIG. 4 shows a cross-section of a femoral component portion of a knee prosthesis according to another embodiment of the present invention.

In one embodiment, femoral component 100 of a knee prosthesis for use with a patient may comprise: a body 102 having a first surface 102A and a second surface 102B; and a rib element 104 protruding from the first surface 102A of the body. Further, the rib element 104 may be elongated along a first axis "A"; the rib element 104 may comprise a free edge; and the free edge of the rib element 104 may comprises a bulbous terminus 106 along at least a portion of the length of the rib element 104 (see also, the cross section of FIG. 4, showing body 102' having a first surface 102A' and a second surface 102B'; and a rib element 104' protruding from the first surface 102A' of the body; further, the rib element 104' may comprise a free edge; and the free edge of the rib element 104' may comprises a bulbous terminus 106' along at least a portion of the length of the rib element 104'). Further, femoral component 100 may comprise fixation lug 108 (such a fixation lug may be of any desired shape (e.g., rectangular, pyramidal, tapered)).

In one example, first surface 102A may be a bone-facing surface and the second surface 102B may be an articulation surface.

In another example, the second surface 102B may be an articulation surface for articulation against a tibial component of the knee prosthesis.

In another example, the furthest distance that the bulbous terminus 106, 106' protrudes from the first surface may be less than about 6 mm.

In another example, the body 102 may be elongated along a second axis "B".

In another example, the first axis A and the second axis B may be essentially parallel, such that the rib element 104 (and the bulbous terminus 106) is elongated in essentially the same direction as the body 102.

In another example, each of the first axis "A" and second axis "B" may run in an essentially anterior-posterior direction.

In another example, the bulbous terminus 106,106' may be the widest portion of the rib element.

In another example, the bulbous terminus 106,106' may be wider than at least an intermediate portion of the rib element that is situated between the bulbous terminus 106,106' and the first surface of the body.

In another example, the bulbous terminus 106,106' may add rigidity to the femoral component.

In another example, the bulbous terminus 106,106' may be configured to be held by bone cement disposed in a femur bone of the patient.

In another example, the rib element may extend across the first surface of the body essentially an entire distance of the first surface of the body from a first end of the first surface of the body to a second end of the first surface of the body.

In another example, the rib element may extend across the first surface of the body less than an entire distance of the first surface of the body from a first end of the first surface of the body to a second end of the first surface of the body.

In another example, the first end of the first surface of the body may be an anterior end of the body and the second end of the first surface of the body may be a posterior end of the body.

In another example, the bulbous terminus may extend essentially the entire length of the free edge of the rib element.

In another example, the bulbous terminus may extend less than the entire length of the free edge of the rib element.

In another example, the first surface 102A of the body may comprise a concave portion.

In another example, the second surface of the body 102B may comprise a convex portion.

In another example, the femoral component may be used in one of: (a) a unicondylar knee replacement procedure; and (b) a tricompartmental knee replacement procedure.

In another example, the rib element may be a central rib element (e.g., centered along an elongated axis of the femoral component).

In another example, the rib element may be of modest height with a crossection containing a bulbous terminus that runs almost the entire anterior/posterior (A/P) length of the femoral component (this rib element may confer significant stiffness and strength to the femoral component.).

In another example, a shell-like structure or rim along the perimeter (the full perimeter or part of the perimeter) of the femoral component (see, e.g., element 410 in the cross sectional view of FIG. 4) may also confer significant stiffness and strength to the femoral component.

Figure 3A:
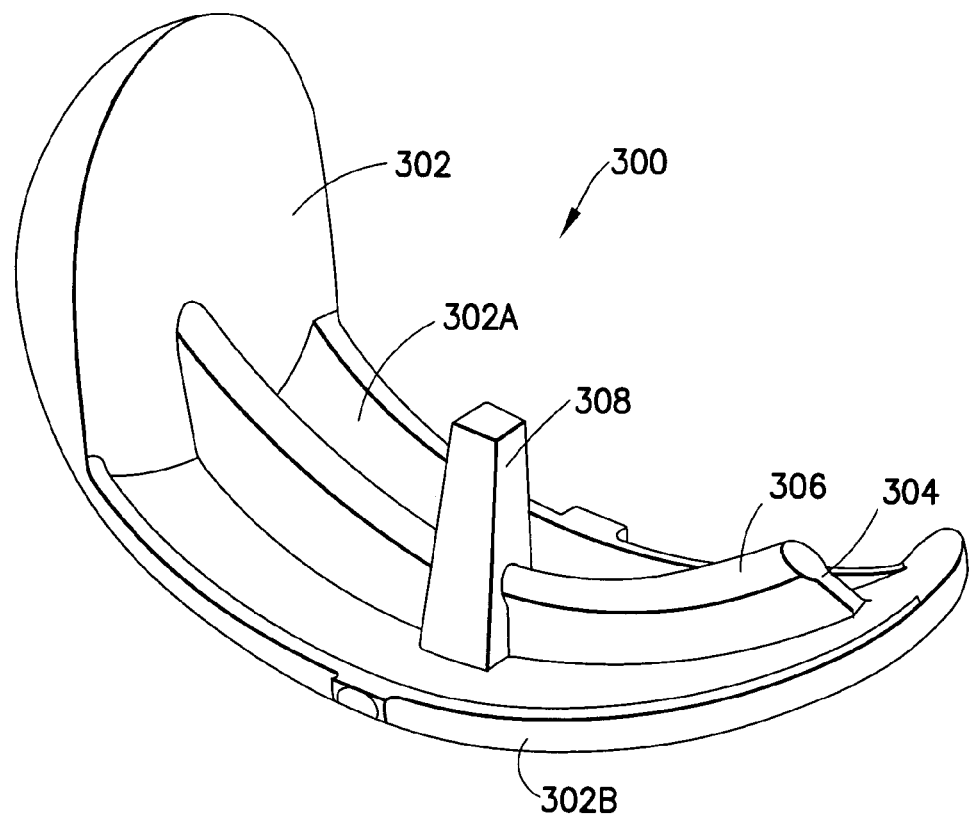
FIGS. 3A and 3B show, respectively, a bottom and side view of a femoral component portion of a knee prosthesis according to another embodiment of the present invention.
Figure 3B:
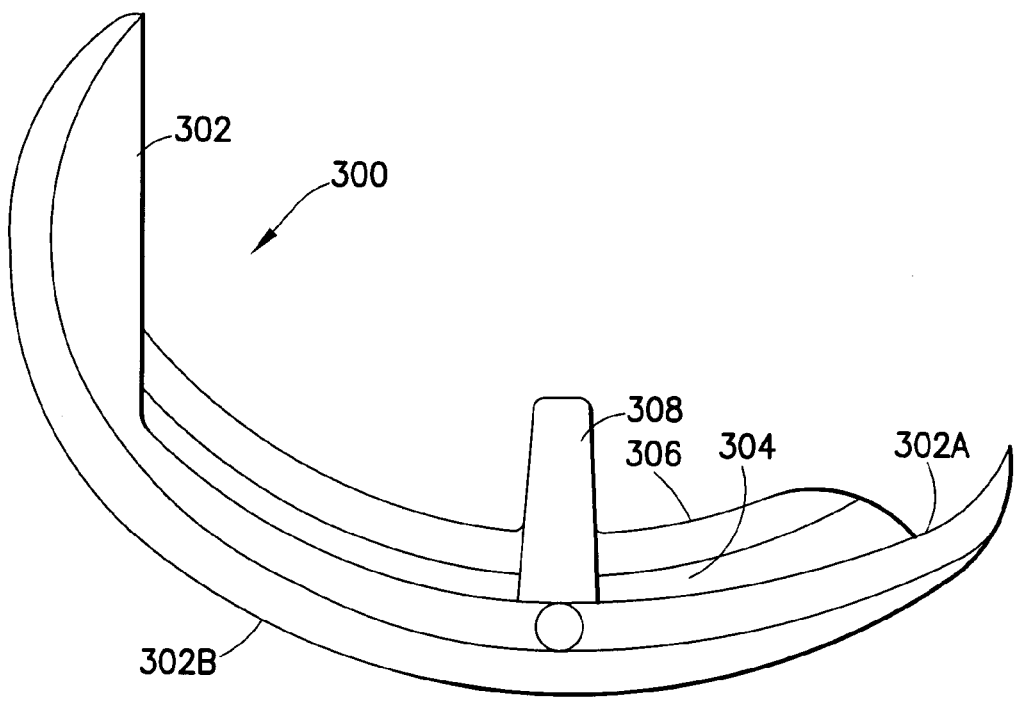

Referring now to FIGS. 3A and 3B, it is seen that these Figs. show, respectively, a bottom and side view of a femoral component 300 portion of a knee prosthesis according to another embodiment of the present invention. As seen in these Figs. femoral component 300 may comprise: a body 302 having a first surface 302A and a second surface 302B; and a rib element 304 protruding from the first surface 302A of the body. Further, the rib element 304 may comprise a free edge; and the free edge of the rib element 304 may comprises a bulbous terminus 306 along at least a portion of the length of the rib element 304. Further, femoral component 300 may comprise fixation lug 308.

Figure 5:
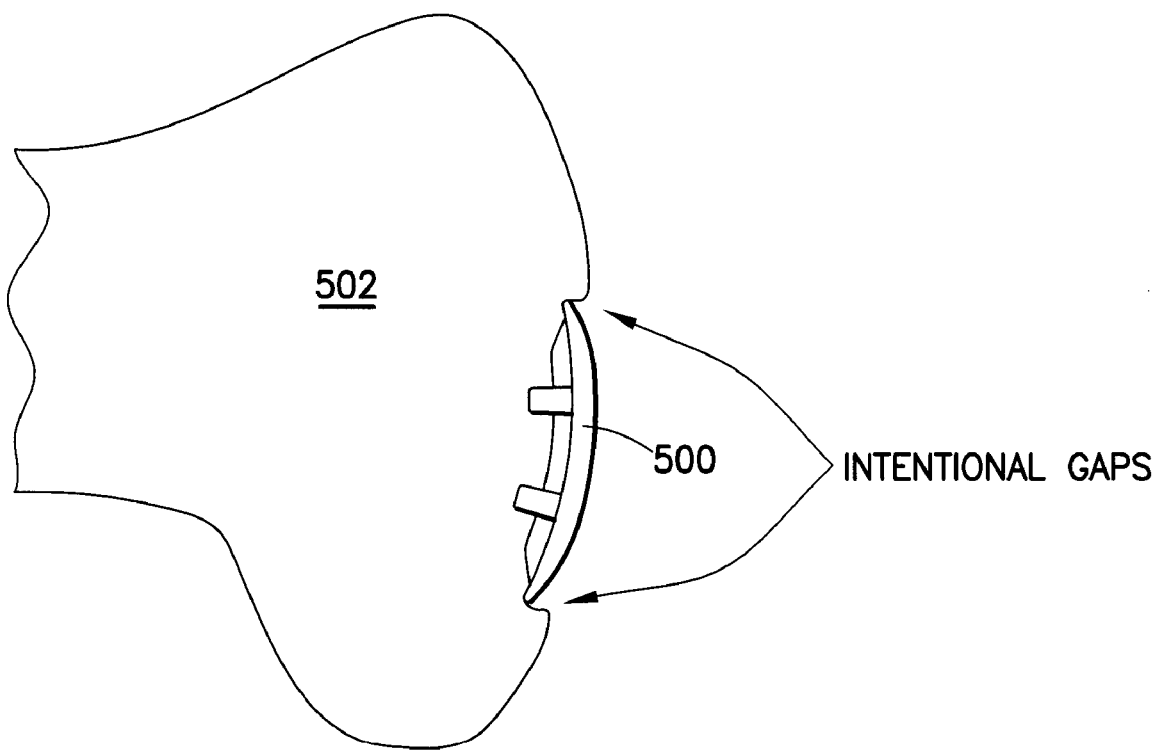
FIG. 5 shows a side view of a femoral component according to another embodiment of the present invention as applied to a femur bone (insetting and/or use of intentional gaps may avoid or minimize edge loading).

Referring now to FIG. 5, this Fig. shows a side view of a femoral component 500 according to another embodiment of the present invention as applied to a femur bone 502 (insetting and/or use of intentional gaps may avoid or minimize edge loading);

Referring now to FIG. 6, this Fig. shows a side view of a femoral component 600 according to another embodiment of the present invention as interfacing with a corresponding tibial component 650. As seen in this Fig., femoral component 600 may comprise: a body 602 having a first surface 602A and a second surface 602B; and a rib element 604 protruding from the first surface 602A of the body. Further, the rib element 604 may comprise a free edge; and the free edge of the rib element 604 may comprises a bulbous terminus 606 along at least a portion of the length of the rib element 604. Further, femoral component 600 may comprise fixation lugs 608A,608B.

Figure 7A:
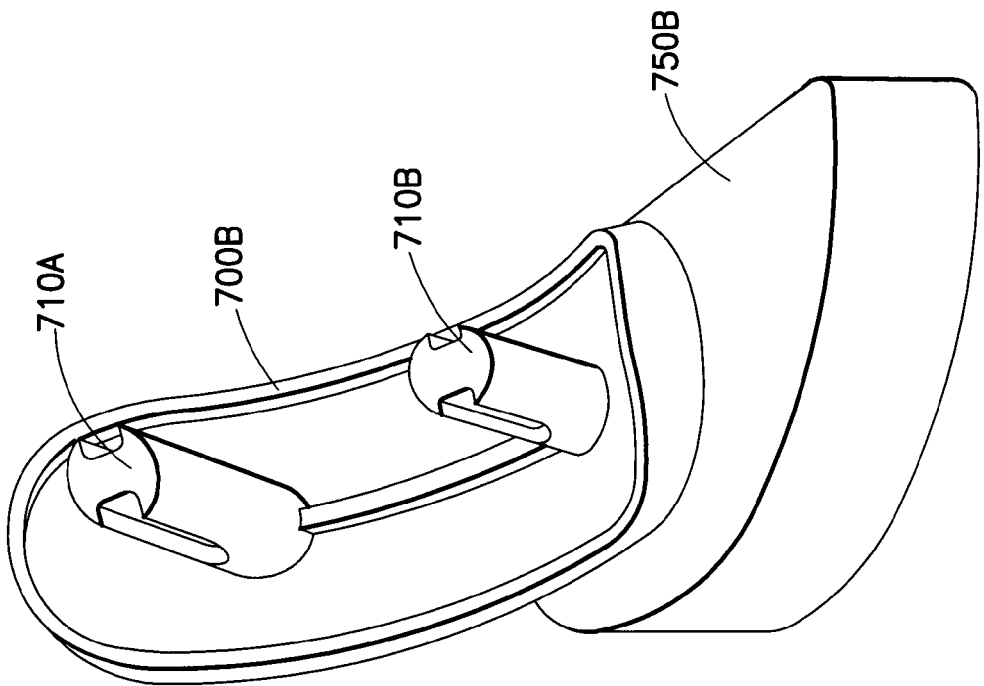
FIGS. 7A and 7B show other views of femoral components according to embodiments of the present invention as interfacing with corresponding tibial components.
Figure 7B:
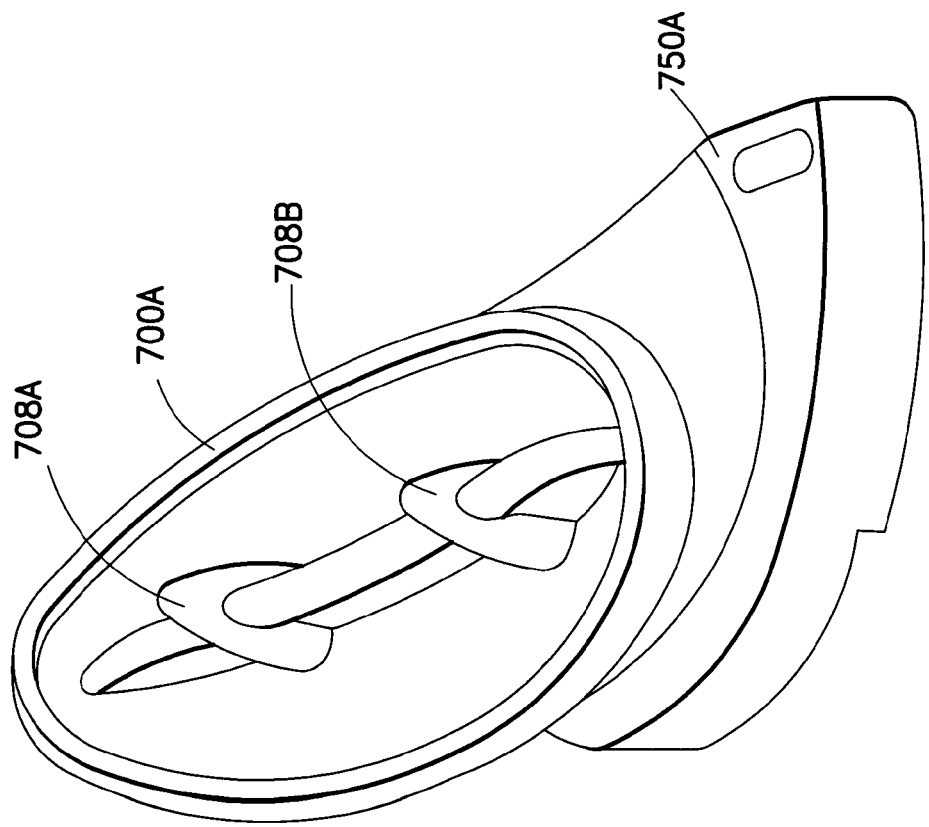

Referring now to FIGS. 7A and 7B, these Figs. show other views of femoral components 700A, 700B according to embodiments of the present invention as interfacing with corresponding tibial components 750A,750B. As seen in these Figs., femoral component 700A may comprise "pointed" fixation lugs 708A,708B and femoral component 700B may comprise "slotted" fixation lugs 710A,710B.

Figure 8A:
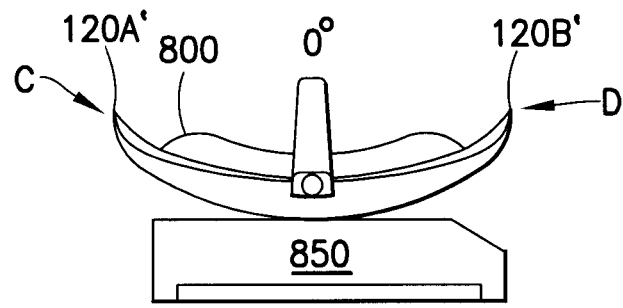
FIGS. 8A-8C show other views of a femoral component according to an embodiment of the present invention as interfacing with a corresponding tibial component (these views show an example femoral component range of motion (ROM) of approximately 60 degrees—as seen, FIG. 8A shows 0 degrees motion.
Figure 8B:
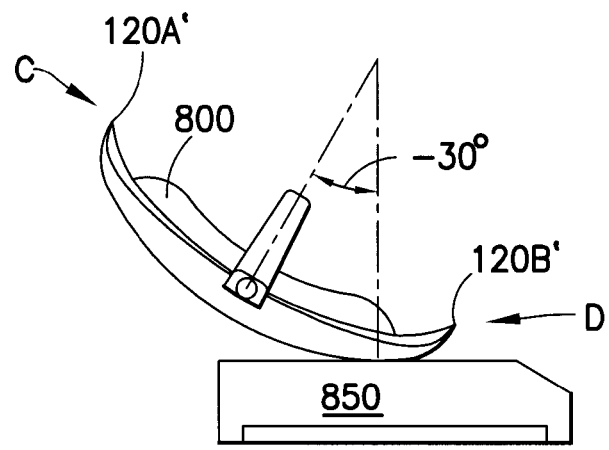
Figure 8C:
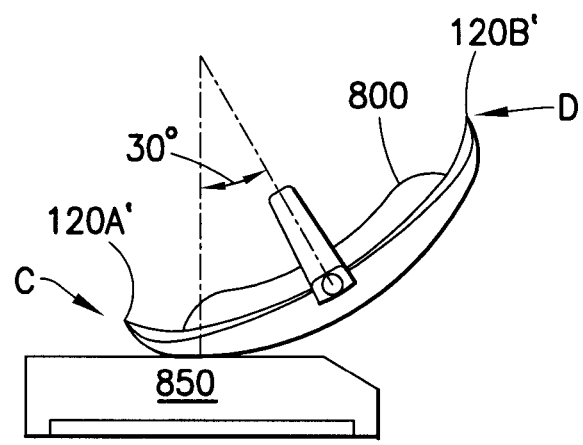

Referring now to FIGS. 8A-8C, these Figs. show other views of a femoral component 800 according to an embodiment of the present invention as interfacing with a corresponding tibial component 850 (these views show an example femoral component range of motion (ROM) of approximately 60 degrees—as seen, FIG. 8A shows 0 degrees motion; FIG. 8B shows −30 degrees of motion; and FIG. 8C shows 30 degrees of motion).

Referring now to FIGS. 9A and 9B, these Figs. show other views of a femoral component 900A according to an embodiment of the present invention (FIG. 9A is a side view and FIG. 9B is cross section taken through line I-I of FIG. 9A; in addition, it is noted that these FIGS. 9A and 9B show a femoral component 900A with anterior and posterior "claws" 901A,901B according to an embodiment of the present invention (drawn in these Figs. with a darker line) overlaid with a conventional unicompartmental femoral component 900B without such "claws" (drawn in these Figs. with a lighter line)).

In another embodiment, a femoral component 100 of a knee prosthesis for use with a patient may be provided, comprising: a body 102 having a first surface 102A, a second surface 102B, an anterior end "C" and a posterior end "D"; wherein a first claw portion 120A of the body 102 is disposed at the anterior end "C" of the body 102; wherein a second claw portion 120B of the body 102 is disposed at the posterior end "D" of the body 102; wherein the first claw portion 120A of the body 102 is configured to dig into tissue of the patient (e.g., cartilage and/or bone (e.g., femur bone)); and wherein the second claw portion 120B of the body 102 is configured to dig into tissue of the patient (e.g., cartilage and/or bone (e.g., femur bone)). See, also, for example, first claw portion 120A' of FIGS. 8A-8C and second claw portion 120B' of FIGS. 8A-8C).

In another example, the first claw portion of the body may be configured to dig into bone of the patient through cartilage of the patient and/or the second claw portion of the body may be configured to dig into bone of the patient through cartilage of the patient.

In another example, the first claw portion of the body may be configured to dig into cartilage of the patient (that is, cartilage but no bone) and/or the second claw portion of the body may be configured to dig into cartilage of the patient (that is, cartilage but no bone).

In another example, the first surface 102A may be a bone-facing surface and the second surface 102B may be an articulation surface.

In another example, the second surface 102B may be an articulation surface for articulation against a tibial component of the knee prosthesis.

In another example, the body 102 may be elongated along an axis connecting the anterior end "C" of the body 102 and the posterior end "D" of the body 102.

In another example, the first surface 102A of the body may comprise a concave portion.

In another example, the second surface 102B of the body may comprise a convex portion.

In another example, the femoral component may be used in one of: (a) a unicondylar knee replacement procedure; and (b) a tricompartmental knee replacement procedure.

In another embodiment, a femoral component of a knee prosthesis for use with a patient is provided, comprising: a body having a first surface, a second surface, an anterior end and a posterior end; and a rib element protruding from the first surface of the body; wherein a first claw portion of the body is disposed at the anterior end of the body; wherein a second claw portion of the body is disposed at the posterior end of the body; wherein the first claw portion of the body is configured to dig into tissue of the patient (e.g., cartilage and/or bone (e.g., femur bone)); wherein the second claw portion of the body is configured to dig into tissue of the patient (e.g., cartilage and/or bone (e.g., femur bone)); wherein the rib element is elongated along a first axis; wherein the rib element comprises a free edge; and wherein the free edge of the rib element comprises a bulbous terminus along at least a portion of the length of the rib element.

In another embodiment, the present invention marries arthroscopic technology with conventional joint reconstruction principles. This "best of both world" approach addresses the minimally invasive surgery needs while providing the patient with an implant that is likely more functional and/or durable than conventional alternatives.

Figure 10:
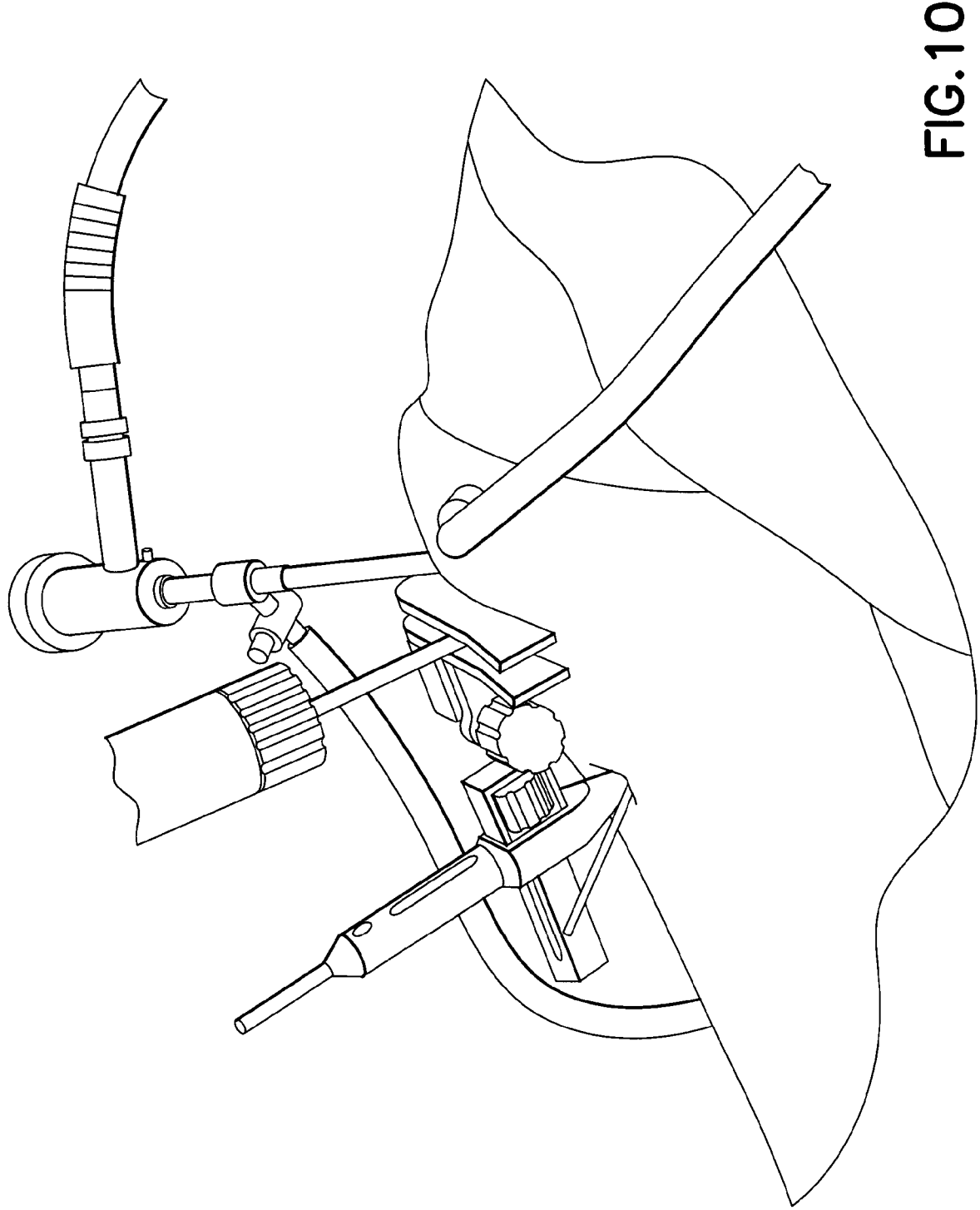
FIG. 10 shows a view of utilization of a burr guide and other instrumentation according to an embodiment of the present invention.
Figure 11:
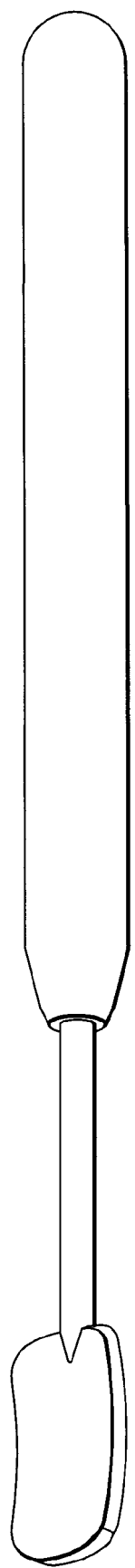
Figure 12:
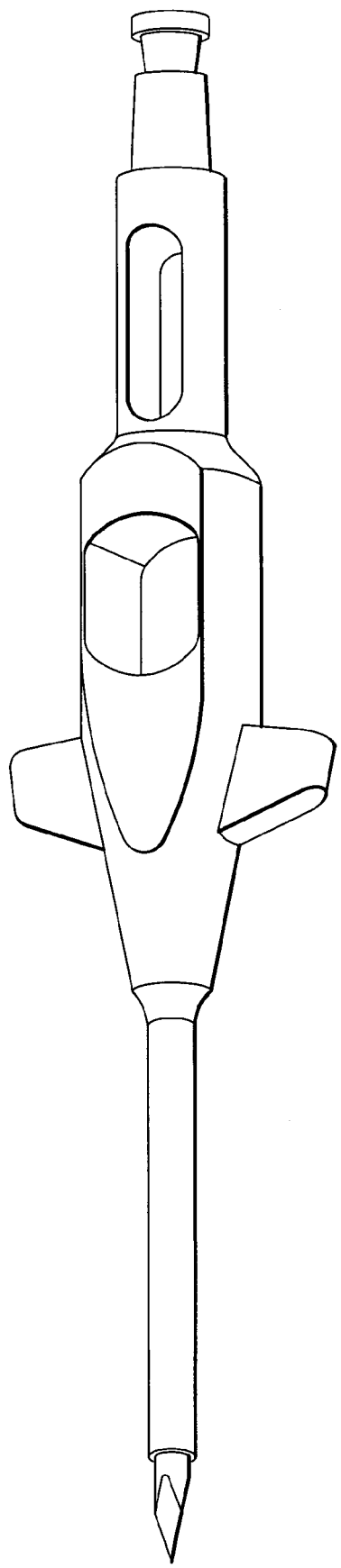
Figure 13:
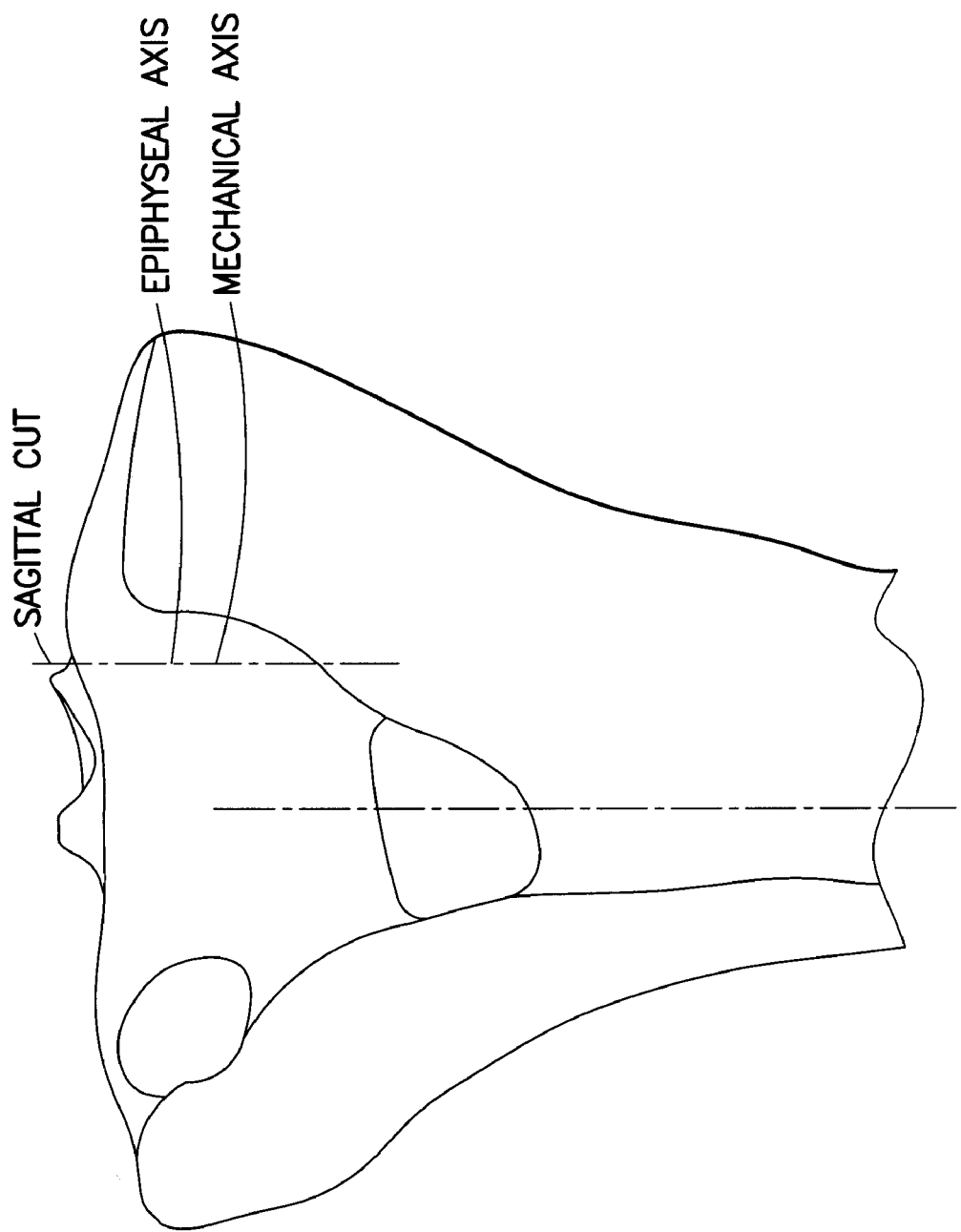
Figure 14B:
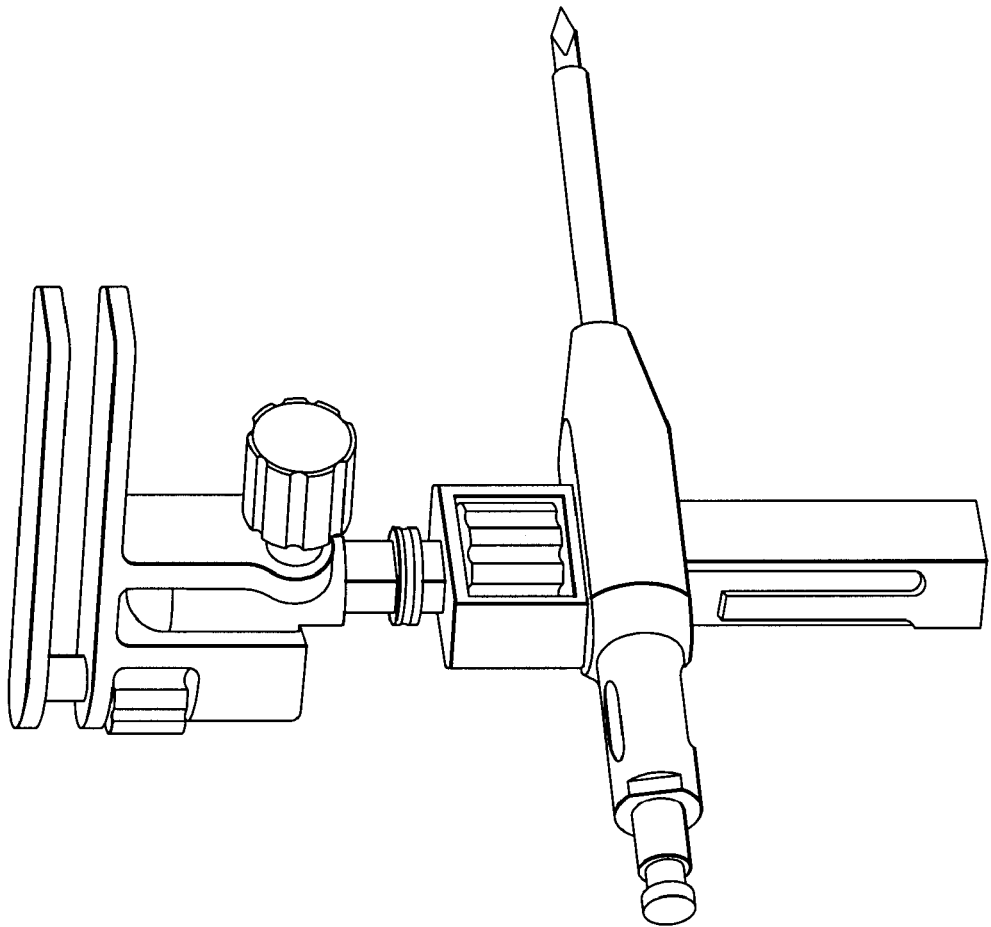
Figure 14A:
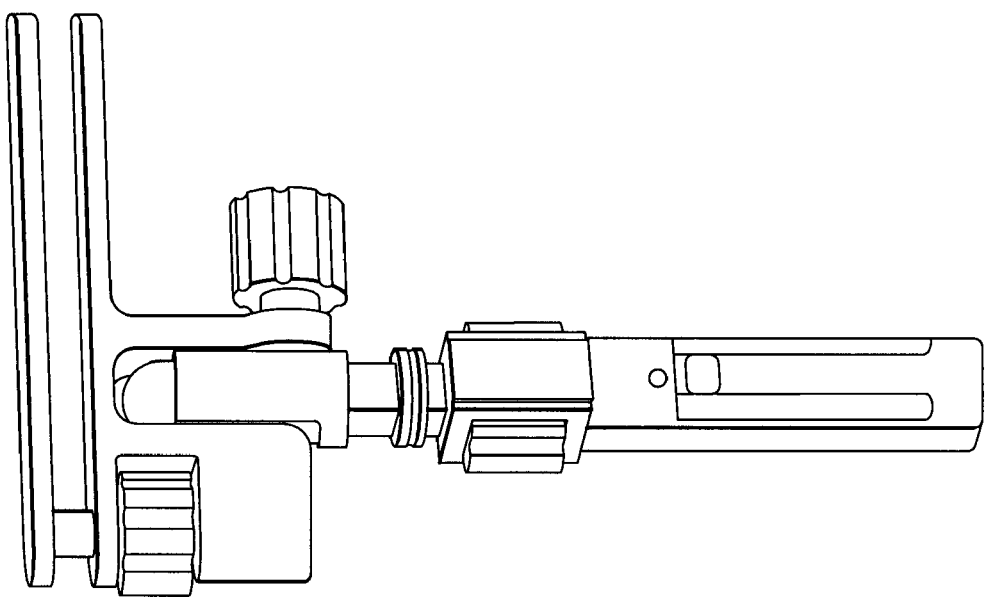
Figure 15:
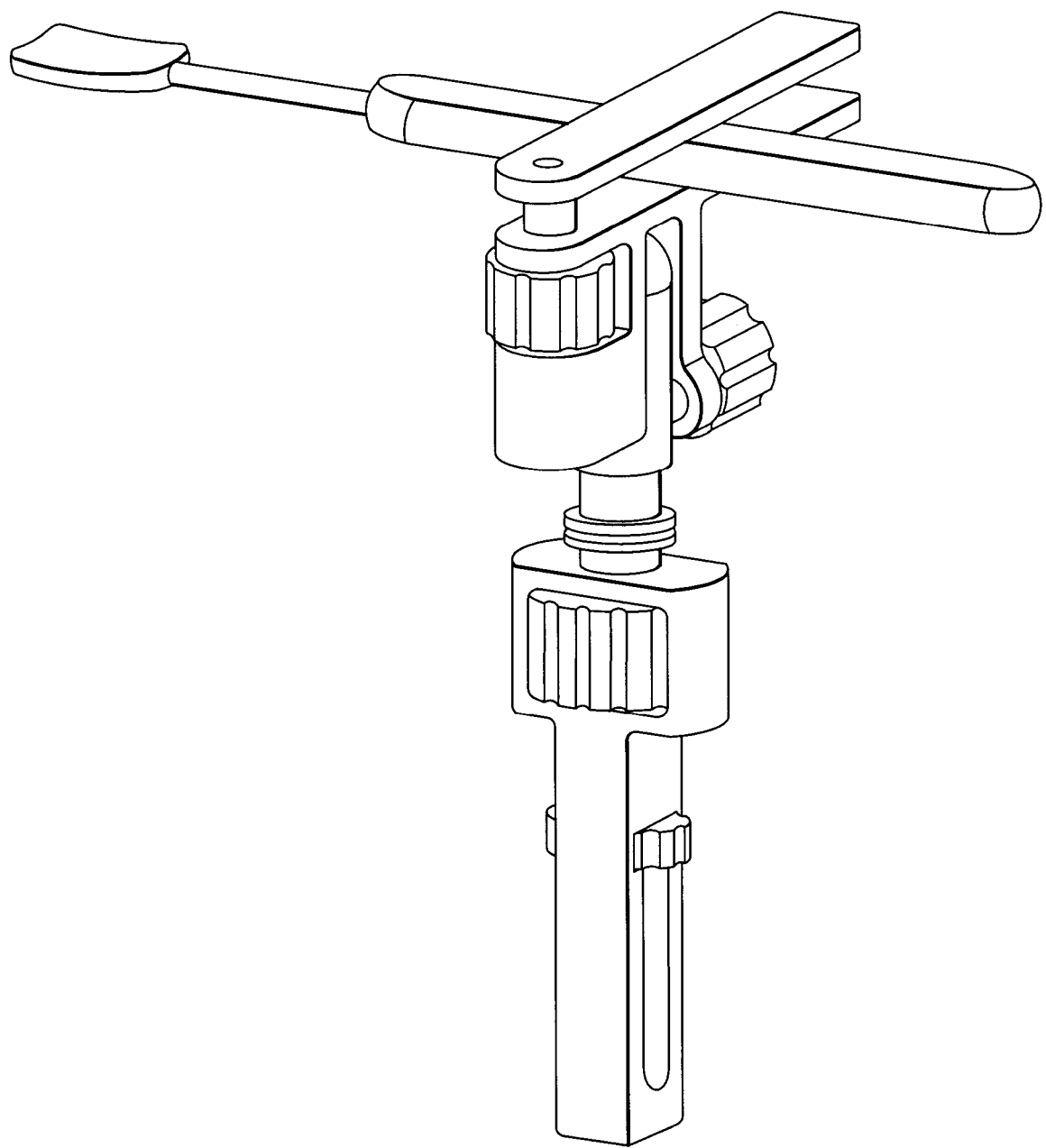
Figure 16:
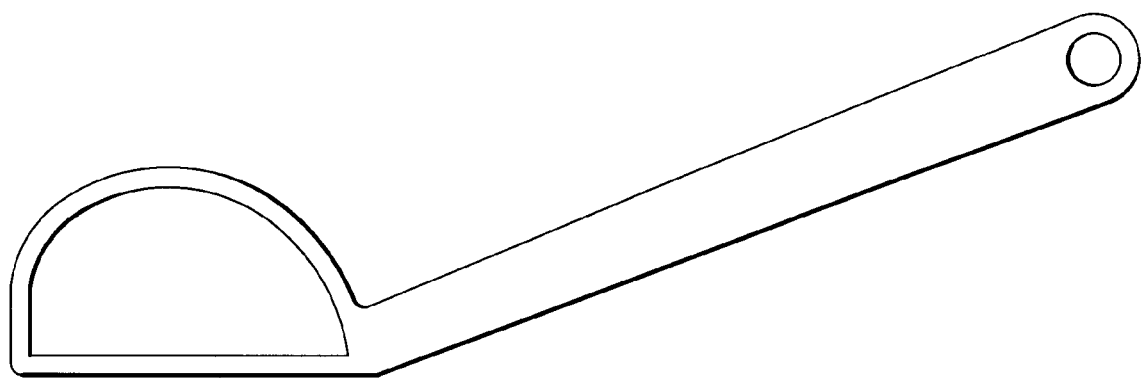
Figure 17:
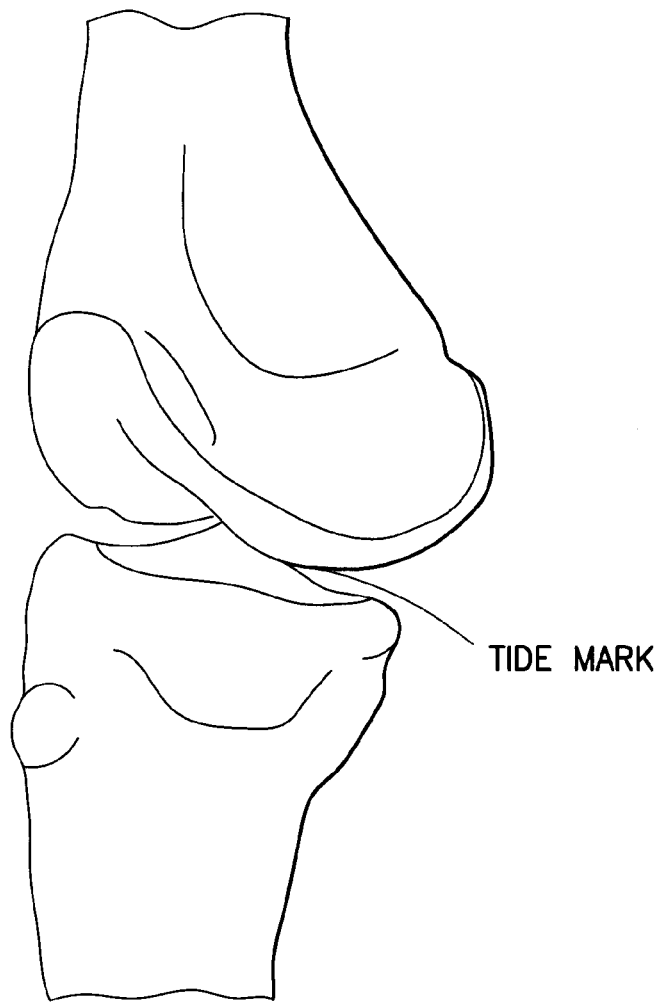
Figure 18:
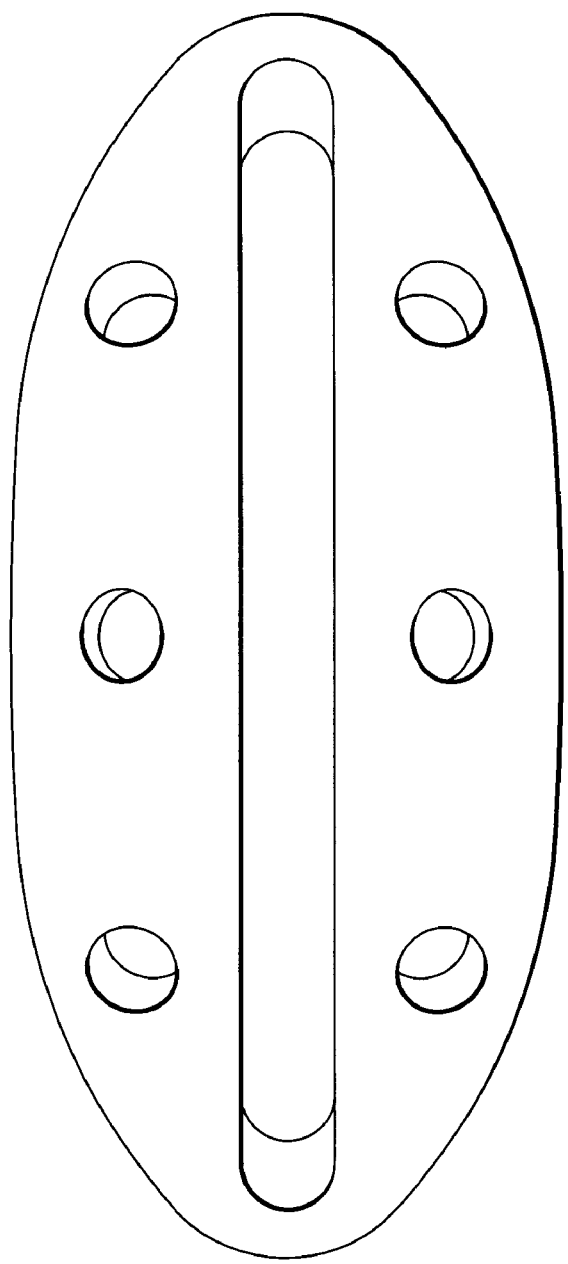
Figure 19:
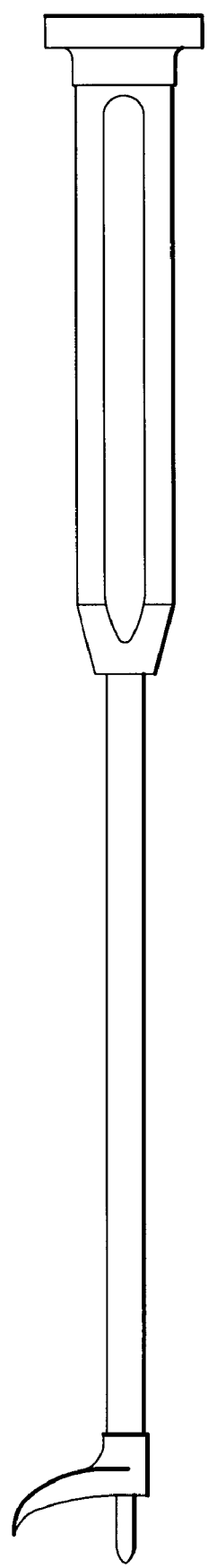
Figure 20:
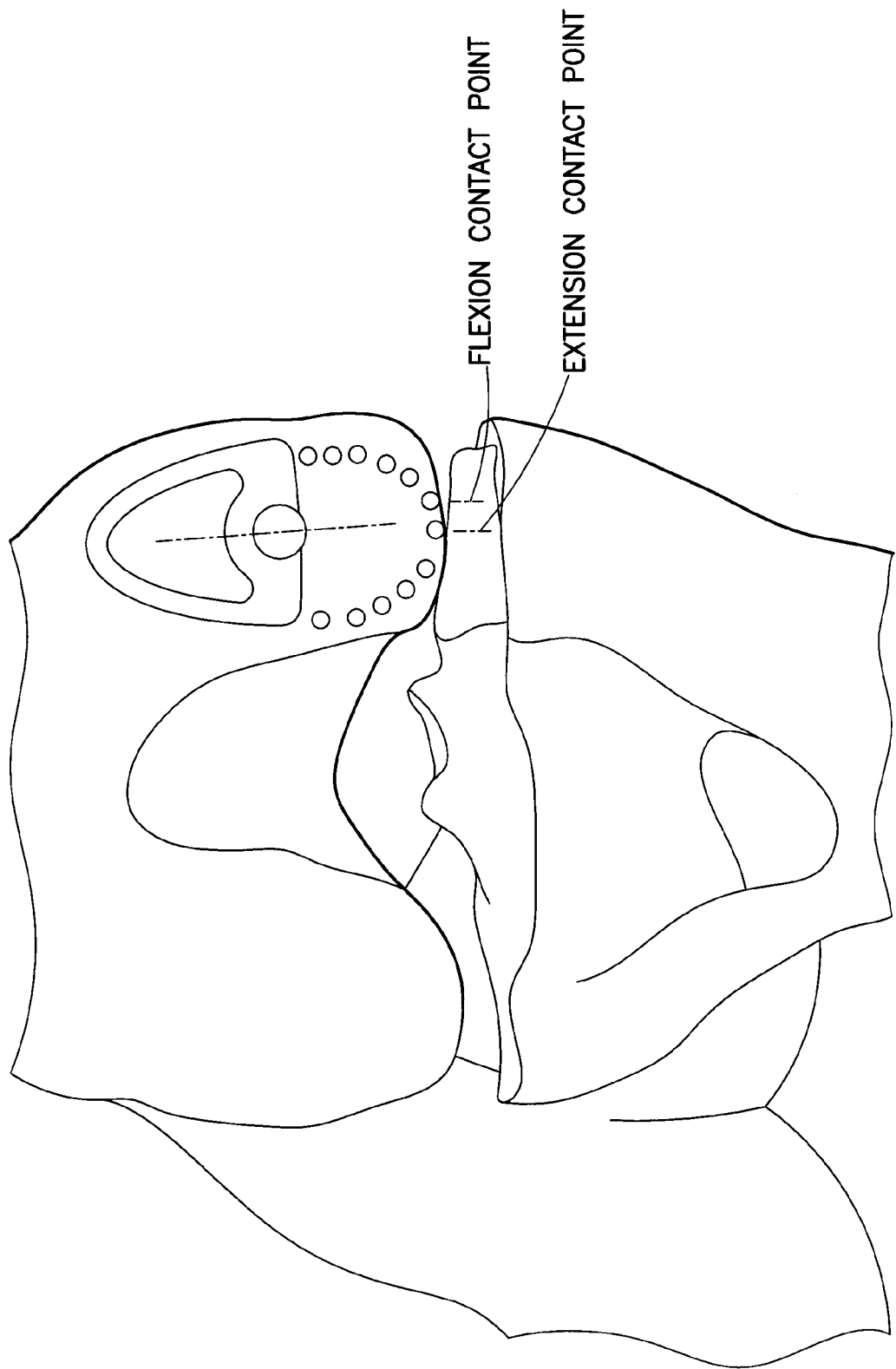
Figure 21:
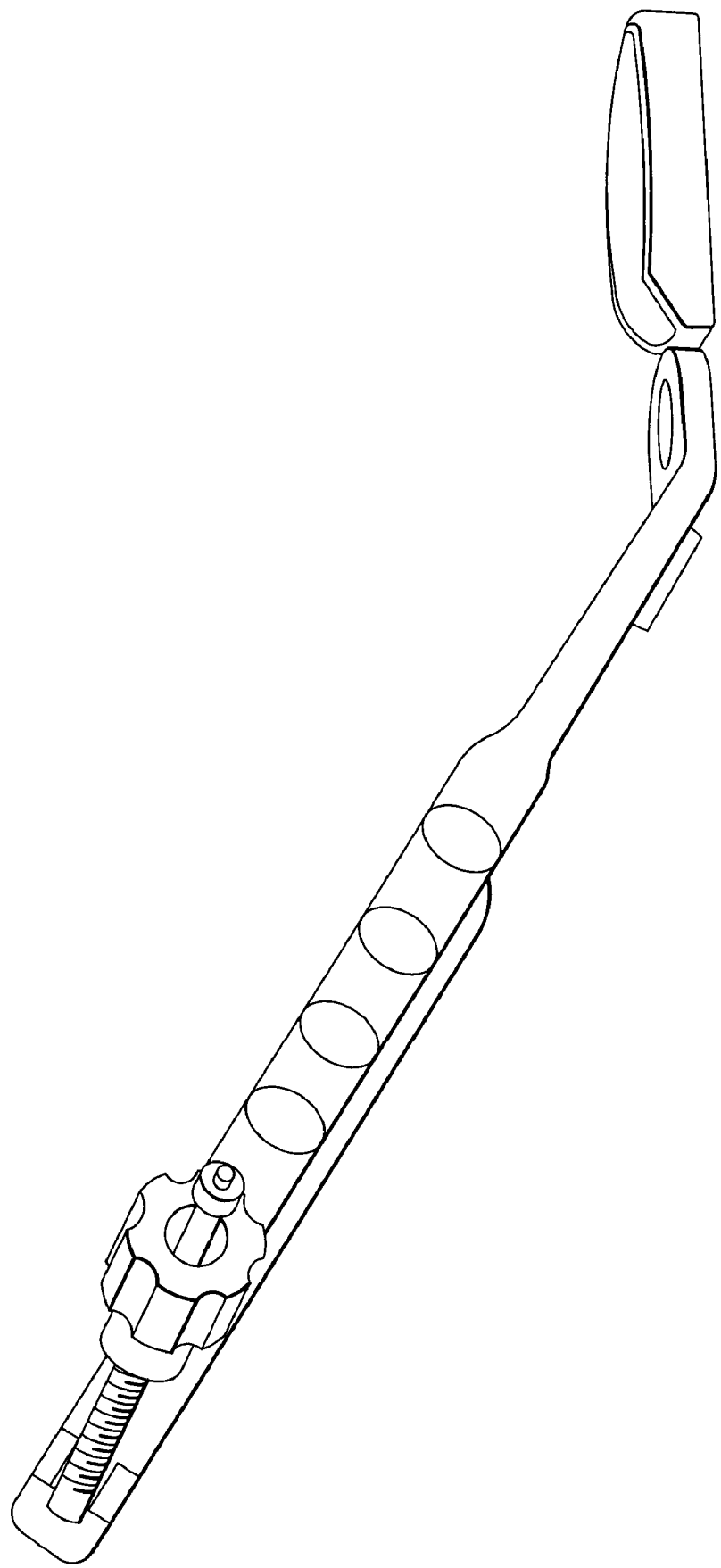
Figure 22:
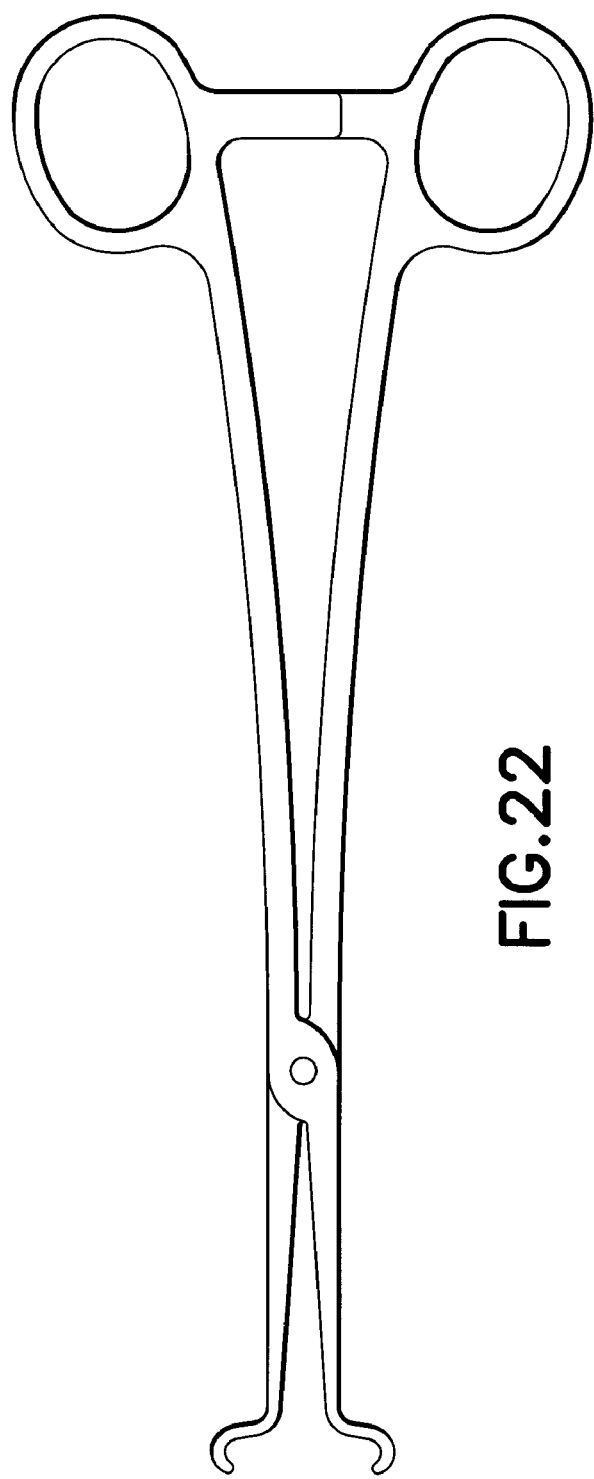
Figure 23:
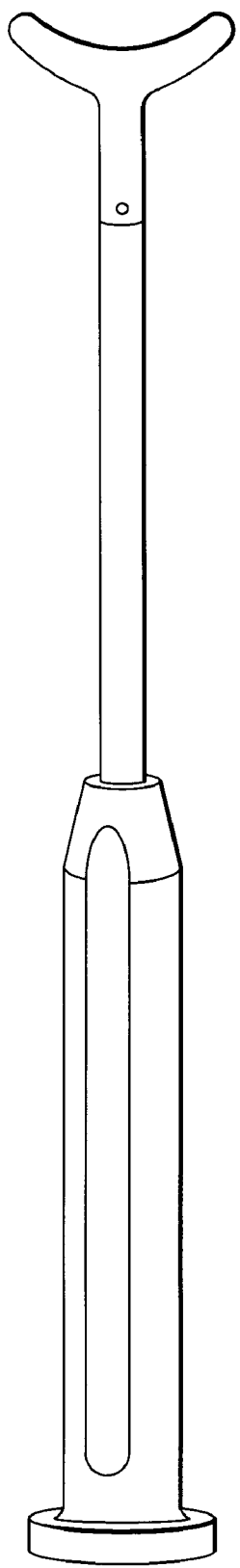
Figure 27:
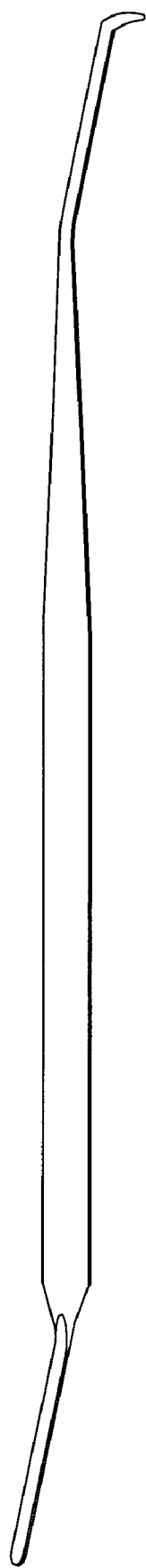
Figure 28:
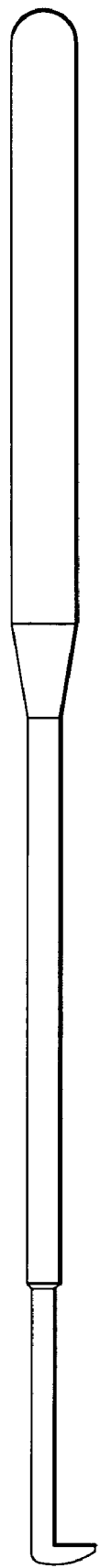

In one example, a surgical technique (see, e.g., the instrumentation of FIG. 10 that may be used in this technique) may provide for the bone to be partially prepared "closed" (i.e. arthroscopically) with burrs, routers and/or templates and then preparation may be finished "open" using conventional knee arthroplasty techniques. In this regard:

The "hybrid" technique is very effective since arthroscopy provides excellent visualization during the bone preparation and the incision size can be kept minimal during final bone preparation and cementation.

Bone preparation with a burr guide provides a method to produce a flatter more controlled surface than does preparing the bone in a free-hand manner.

As described herein, various embodiments of the present invention may provide an implant system, surgical technique and instruments that enable a surgeon to perform a limited arthroplasty on patients who are afflicted with early stages of knee joint arthritis. This system of implants, techniques and instruments may be minimally invasive—e.g., to reduce the patient's pain and rehabilitation and so that if/when the knee arthritis again produces the recognized symptoms of progressive degeneration a revision operative procedure can be performed using a conventional tricompartmental knee. In one example, the technique may be based upon the standard surgical technology used in the practice of Sports Medicine (in this regard, it is believed that surgeons skilled in the practice of Sports Medicine are typically adept at arthroscopic techniques and typically prefer the visualization and precision this equipment provides as compared to conventional instrumentation typically used in an "open" technique.).

The "marriage" of "open" and "closed"—based implants, surgical techniques and instrumentation provided by various embodiments of the present invention may enable the surgeon to prepare the tibia and femur arthroscopically. This improves visualization and accuracy while minimizing the trauma to the patient. Completing, for example, almost all of the bone shaping arthroscopically enables the surgeon to reduce the secondary incision that is necessary for completing the bone preparation and for positioning and affixing the implant as compared to the incision size if the procedure was only completed in an "open" fashion. Adding an "open" portion to the surgical technique enables the surgeon to perform the important final bone preparation, cementation and implant assembly to the bone more reliably, thereby increasing the implant's survival probability.

Of note, conventional attempts have typically taken either one of two approaches:

1. The entire procedure is completed "closed" (i.e. arthroscopically)

2. The entire procedure is completed "open" but with a minimal incision

It is believed that a shortcoming of the former is that when using the procedure it was difficult to accomplish the precise cuts that are necessary for proper implant fit. In addition, it is believed that the procedure was difficult to complete (e.g., to complete the final cementation of the implants). Of course, any time a surgical technique is difficult it typically results in minimal acceptance by surgeons and increased clinical failure for those surgeons that chose to attempt the procedure. Moreover, it is believed that the implants used for this procedure were also typically bulky, therefore requiring excess bone to be removed which often required more expensive and bulky "revision" knees to be used when the index operation had to be revised.

Further, it is believed that a shortcoming of the latter is that the incision is made larger (the large size of the incision is required to accept the typical bulky instruments used to guide the required cuts) and the procedure typically includes dissection of soft connective tissues to allow for the insertion of the typically bulky instruments. This larger incision typically leads to longer recovery times for the patient as compared to what is anticipated with various embodiments of the invention disclosed (e.g., because the larger incision typically requires the cutting of subcutaneous ligaments, tendons and muscle tissue, a longer recovery time was required for the patient compared to what is anticipated with various embodiments of the invention disclosed).

One benefit of this embodiment of the invention is that the "marriage" of the arthroscopic instrumentation and techniques with conventional joint reconstruction principles provides, for example, the Sports Medicine surgeon with a surgical procedure consistent with his/her existing operative skills and provides better joint visualization while helping to ensure that the bone is prepared accurately and the implant is positioned well and affixed reliably so that it remains stable. All of this may be accomplished, for example, with minimal trauma to the patient and with minimal bone loss. Additionally, the application of sound implant design principles that have historically led to successful joint arthroplasty results to this surgical procedure may increase the likelihood of clinical success for this at least partially minimally invasive procedure.

Reference will now be made to FIGS. 11-28. These FIGS. 11-28 show various instrumentation (and applications thereof) in connection with another example surgical technique according to an embodiment of the present invention.

More particularly, this example surgical technique relates to a mini-open surgical technique for the medial compartment. This surgical technique may be applied as follows:

1. Scope the knee joint to view the damaged medial compartment as well as the intact lateral and patellofemoral compartments. At this time is possible to treat meniscus or cartilage damages and judge if the procedure is appropriate.

2. Expose the medial side of the joint using a midline or medial parapatellar incision. Undermine the skin and soft tissues. Perform a medial arthrotomy.

3. First use the meniscus as a reference for the joint line height when the tibial trial will be inserted. Remove the medial meniscus so that the tibial cortical rim is seen on the degenerated side. A meniscal resector or similar instrument may be used to remove the meniscus.

4. Insert the Alignment Probe (see FIG. 11) into the joint. This instrument can help in assessing frontal plane tibial alignment and tibial slope, which should mimic the natural epiphyseal axis and slope of the proximal tibia. The alignment probe is better inserted in extension and not in flexion because of the posterior translation of the femur with knee flexion.

5. Insert the Burr Guide Pin (see FIG. 12) slightly distal and medial to the tibial tubercle, making sure to get good bone purchase without violating the pes anserinus. The threaded portion should be bicortical to the tibia making sure not to extend past the posterior tibia. Use the Alignment Probe inserted in the Burr Guide to decide the distance of the Burr Guide Pin to the joint line and also to determine the frontal plane alignment. You could also use the external alignment rod to align the device. Drive K-wire(s) into the bone to prevent rotation. The Burr Guide Pin should be aligned to the epiphyseal axis for minimal bone removal of the tibia. The mechanical axis can also be referenced. However, the patient's normal anatomy should also be taken into consideration (see FIG. 13). An ankle clamp and tibial resector shaft with a tibial cutting block may be used instead of the Burr Guide and Pin.

6. Assemble the Burr Guide to the Burr Guide Pin (see FIGS. 14A and 14B). The Burr Guide is adjustable proximal/distal as well as in the sagittal plane to position the proper posterior slope. Cutting slot gap is also adjustable which you can adjust by rotating the notch (see FIG. 15). A plastic height indicator can be moved up and down; each mark is 1 mm apart.

7. It is advised to begin with the tibia first, so the posterior condyle of the femur can be accessed and visualized better. Remove 2-4 mm of bone from the tibia. The amount of cartilage will vary, but will be around 2 mm for normal (non-deteriorated) cartilage. The depth of the tibial cut can be determined by:

a. Place the plastic height indicator on the Burr Guide at the base (so it can no longer move farther down); move the indicator up one tic for each millimeter of bone to be removed (i.e. if 3 mm of tibia should be removed, move the plastic indicator up 3 places).

b. Perform a notchplasty on the medial femoral condyle and the tibial spine. Use a rasp being careful to not be overly aggressive.

c. Use a saggital saw to first cut next to the tibial spine. The direction of the cut should be parallel to the tibial crest while also touching the tibial spine, being careful not to damage the ACL attachment. The top plate of the Burr Guide can assist in limiting the depth of the cut.

d. Use an oscillating saw to cut the proximal tibia, using the Burr Guide to help guide the cut (in one example, the epiphysis or mechanical axis may be used as a guide).

8. The top plate of the Burr Guide can assist in cutting the proximal tibia.

a. The Tibial Template Guide (see FIG. 16) can be used to assess the size and correct amount of bone removal. The flat edge should touch the tibial spine.

Of note, a nerve hook (see FIG. 28) may help the surgeon determine the amount of bone removal and A/P tibial size 9. Use an electrocautery device to mark the tide mark on the distal femur after having inserted the tibial trial (see FIG. 17).

a. To find the tide mark, place the knee in extension. Define where the anterior tibia touches the anterior femur. The anterior location on the femur just above (or proximal to) where the tibia touches is the tide mark.

10. Put the knee in back into flexion. Pick the appropriate size Femoral Fin Guide (see FIG. 18). Check the size to make sure it covers the defect and does not extend too far posteriorly; align the anterior inner surface edge with the tide mark. Assess the rotation and positioning of the Femoral Fin Guide. This can best be done with the tibial trial in place. A small holding pin should be placed in one of the two anterior holes. The knee can be taken through a range of motion, allowing the posterior end of the Femoral Fin Guide to rotate into position as it articulates with the tibial trial. The proper position of this guide should be determined by:

A/P: the anterior tip aligns with the tide mark while the posterior tip freely rotates about the holding pin.

M/L: the lateral side of the template should be adjacent to the tibial spine.

Rotation: the lateral edge of the template should be parallel in both extension and flexion with the tibial spine.

Once the proper Femoral Fin Guide is determined, a drill bit can be used to prepare the central hole or a methyl blue marker can mark the central fin (or rib). This will help when positioning the claw tamp.

11. Take the Femoral Claw Tamp (see FIG. 19) and align the claw with the tide mark on the femur. The femoral implant should not be anterior to the tide mark. Look at the M/L width of the Femoral Claw Tamp on the bone to determine the best size. Rotate the Femoral Claw Tamp 180° degrees to check the posterior aspect. If the size of Femoral Claw Tamp is good, use a mallet to impact the instrument to create an impression anteriorly and posteriorly. Remove the Femoral Claw Tamp from the joint.

12. Burr inside of the outline created by the Femoral Claw Tamp. Start burring at the tide mark and then move posteriorly by flexing the knee (see FIG. 20).

a. Burr 2-3 mm of femoral bone preserving the original geometry (curvature) of the distal femur.

b. Burring from the side (saggital plane) makes it easier to see how much bone is being removed. Depth can be checked with a standard nerve hook which is approximately 3 mm.

13. Place a pin in the anterior hole OR use the femoral holder to stabilize the Femoral Fin Guide. Use a burr to prepare for the central fin (or rib) feature of the femoral component. The burr should prepare a 5 mm deep slot. It may help to remove the tibial trial while preparing for the central fin (or rib).

a. The correct alignment of the Femoral Fin Guide in extension with the tibial trial will also check the thickness of the tibial trial and proper amount of bone resection.

b. Alternatively a drill bit can be used to drill the central hole as well as the extremes for the central fin (or rib). First use a methyl blue pen to mark the position of the central fin (or rib). Then drill the three holes. Remove the Femoral Fin Guide and use an oscillating saw to prepare the central fin (or rib).

14. Insert the Tibial Trial into the joint using the Uni Multi-Tool (see FIG. 21). Insert the Uni Multi-Tool through the two holes on the anterior portion of the tibial trial. Clamp the trial by squeezing the handles and tightening the screw. This will provide the surgeon a good grasp of the component while inserting it into the joint. Extend the knee fully and ensure that the tide mark does not contact the tibial trial. Insert the Cement pressurizer/tensor (FIG. 26). The 1 mm side of the Cement pressurizer/tensor should fit easily between the distal femur (without the femoral trial) and tibial trial. If it does not, additional tibial bone should be removed.

15. Using the Femoral Holder (see FIG. 22), a trial femoral component is placed on the femoral surface.

a. Use the Femoral Pusher (see FIG. 23) to tamp the trial onto bone. Assess the edges to ensure they are all either flush or inset with the bone.

b. Ensure the femoral trial is flush or inset with surrounding bone.

16. Take the knee joint through a range of motion and check varus/valgus stability. With the knee in extension the surgeon should be able to open the medial joint 2-3 mm. Remove the trials once the proper fit and stability is achieved.

(Note: This will be the final phase in sizing of the femur and tibia: here the surgeon will then decide the final poly thickness of the tibia component.)

17. Remove the trials and dry the joint. Begin mixing the bone cement. Open the appropriate implant boxes and packages. Prior to cementing the components, prepare the resected femoral and tibial surfaces with multiple drill holes, pulse lavage and drying.

18. Place cement on the tibial bone surface while in its doughy phase and the undersurface of the tibial component in its sticky phase, making sure cement is in the dovetail undercuts on the tibial component (see FIG. 24). A gloved thumb or the cement pressurizer/tensor can be used to compress the cement.

19. Place cement on the femoral component while in its doughy phase. Use the Femoral Pusher to fully seat the femoral component (see Femoral component in FIG. 25A and Femoral Pusher in FIG. 25B).

20. The Cement Pressurizer (see FIG. 26) is inserted between the femoral and tibial components to pressurize the cement. It is critical that the implants be held steady while the cement cures. Otherwise debonding may occur which can lead to early loosening.

21. Remove any excess cement with the Cement Remover (see FIG. 27). It is critical to properly clean the cement from around all the implant prosthesis especially posteriorly on the tibia. Be sure not to remove cement from the dovetail groove on the medial side of the tibial implant.

22. Close the incision and take the knee through a range of motion.

23. Insert an arthroscopic scope to ensure no excess cement is left in the joint.

In another example, the present invention may be utilized by sports medicine surgeons.

In another example, the present invention may be utilized by joint surgeons (e.g., joint replacement surgeons).

In another example, the patient indicated for the present invention is not overweight and does not expect to resume high loading activities.

In another example, the present invention may be used in the context of an "outpatient" procedure.

In another example, the present invention may be used for younger patients than has typically been the case.

In another example, the present invention provides femoral and/or tibial components that allow for resurfacing of the bone with minimal bone removal so that if degeneration progresses, revision surgery can be accomplished by making standard bone cuts to implant a primary tricompartmental knee.

As described herein, one embodiment of the present invention provides a femoral component of a knee prosthesis, wherein the femoral component includes a sharp radius at each end (e.g., the anterior end and the posterior end) of the femoral component. The sharp radius at each end may form a "claw" at each end. Each of these claws may "dig" through the patient's cartilage into the bone (or may "dig" directly into bone if there is no intervening cartilage). Enhanced fixation may be achieved with the claws "digging" and fixing into the bone as well as the claws providing additional cement pressurization (e.g., with the claws in the bone, cement is less likely to escape by the anterior and posterior ends).

Further, as described herein, one embodiment of the present invention provides a femoral component of a knee prosthesis, wherein the femoral component includes a raised rib. This raised rib may, for example, simultaneously create sufficient implant strength and adequate cement fixation while minimizing the component's thickness (such as, in order to preserve bone needed for a unicompartmental femoral component that is used for patients who have early stage arthritis). Accomplishing all three attributes (i.e. strength, cement fixation and minimal size) simultaneously has typically been difficult because these are competing objectives.

Further, as described herein, one embodiment of the present invention relates to an implant system associated with knee surgery. Another embodiment of the present invention relates to a surgical technique associated with knee surgery. Another embodiment of the present invention relates to instruments associated with knee surgery. In one example, the present invention provides an arthroscopically assisted procedure to serve as a minimally invasive operation to improve the quality of life for patients who have knee pain secondary to single compartment disease but are not candidates for a total knee replacement. Various aspects of the invention provide implants, instruments, trials and surgical techniques that allow for arthroscopic preparation of the joint, at least in part, prior to implantation.

Further, as described herein, embodiments of the present invention may provide femoral and/or tibial components that allow for resurfacing of the bone with minimal bone removal so that if degeneration progresses, revision surgery can be accomplished by making standard bone cuts to implant a primary tricompartmental knee.

Further, as described herein, various embodiments of the present invention may provide for unicondylar or tricompartmental knee replacement femoral/tibial components and/or techniques.

Further, as described herein, various embodiments of the present invention may provide for an implant and/or technique that is relatively less invasive than some conventional implants and/or techniques Further, as described herein, various embodiment of the present invention may provide for an implant and/or technique that may be used in a relatively more forgiving manner than some conventional implants and/or techniques. In this regard, to enable the implant of one embodiment of the present invention to sit flush with the adjacent cartilage the implant's position may be easily directed by the surgeon based on the surrounding joint surface (cartilage). The implant's position then becomes "set" once the cement cures.

Further, as described herein, various embodiments of the present invention may provide an implant with "claws" sharp enough to allow the implant to be impacted in place (which may be more convenient for the surgeon and may result in a greater probability that the tip of each claw will be embedded in cartilage and/or bone (which ensures a smooth transition). In one specific example, the claws may be located on the implant both anteriorly and posteriorly.

Further, as described herein, various embodiments of the present invention may provide a good implant to bone interface.

Further, as described herein, various embodiments of the present invention may provide a transition zone for articulation.

Further, as described herein, various embodiments of the present invention may provide "I"-beam like strength from the use of a rib element with a bulbous terminus.

Further, as described herein, various embodiments of the present invention may provide a short rib (i.e., in height) as a result of the "I"-beam like strength stemming from the use of a rib element with a bulbous terminus (such a short rib may require less bone removal).

Further, as described herein, various embodiments of the present invention may provide a bone cement interlock from the use of a rib element with a bulbous terminus.

In another example, the present invention may provide an implant (e.g., a femoral implant) that may be used without removing the articular cartilage.

In another example, the present invention may provide an implant (e.g., a femoral implant) that may be used in a cemented application and/or a non-cemented application.

In another example, the present invention may provide an implant (e.g., a femoral implant) that may be self-centering (e.g., in a slightly overlarge bone opening).

In another example, the present invention may provide an implant (e.g., a femoral implant) that may be used in a minimally invasive procedure, an "open" procedure and/or a combination thereof.

In another example, the present invention may provide an implant (e.g., a femoral implant) having one or more claws (e.g., an anterior claw and a posterior claw), wherein the claw(s) get under cartilage (when present) and/or dig into bone to help insure continuity (which may aid, for example, in reducing germs).

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Cobalt Chrome, Ti—Al—Nb, Ti-6Al-4V, stainless steel); (f) any combination thereof. Further still, any metal construct may be a machined metal construct. Further still, any number of protrusions (e.g., such as for initial fixation by forming a bond with cement and/or such as for supplemental fixation by forming a bond with cement) may be utilized with a given prosthesis. Further still, any number of female features that increase the cement mantle and/or provide an interlock may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, various embodiments of the present invention may be applied to a medial compartment and/or lateral compartment. Further still, the raised rib (and/or bulbous terminus) may be continuous or discontinuous (e.g., interrupted by one or more fixation lugs or the like). Further still, various embodiments of the present invention may be provided for total knee replacement. Further still, the implant may comprise one or more dimples, indents, apertures, slots or the like for handling the implant with a tool (see, e.g., the central dimple on the side of the implant 100 of FIGS. 1A and 1B (of course, one or more such dimples, indents, apertures, slots or the like may be disposed on one or more sides of the implant)). Further still, any steps described herein may be carried out in any desired order (and any additional steps may be added as desired and/or any steps may be deleted as desired).

What is claimed is:

1. A component comprising:
    a femoral component of a knee prosthesis comprising:
        a bone-facing surface;
        an articulation surface, wherein the articulation surface has a curvature that is configured to mate with a mating articulation surface selected from at least one of a tibial surface, a patellar surface, a tibial component or a patellar component;
        an anterior end of the articulation surface;
        a posterior end of the articulation surface; and
        a claw extending (1) from an abrupt transition in a radius of the curvature, wherein the abrupt transition in the radius occurs in an anterior-posterior plane of at least one of the anterior most distal end of the articulation surface or the posterior most distal end of the articulation surface and (2) from an abrupt transition in a radius of the bone-facing surface, wherein the claw (1) is not configured to mate with the mating articulation surface, and (2) is configured to dig into tissue of a patient.

2. The component of claim 1, wherein the claw is configured to dig into bone of the patient through cartilage of the patient.

3. The component of claim 1, wherein the claw is configured to dig into cartilage of the patient.

4. The component of claim 1, wherein the articulation surface articulates against a tibial component of the knee prosthesis.

5. The component of claim 1, wherein the bone-facing surface comprises a concave portion.

6. The component of claim 1, wherein the articulation surface comprises a convex portion.

7. The component of claim 1, wherein the femoral component is used in one of: (a) a unicondylar knee replacement procedure; and (b) a tricompartmental knee replacement procedure.

8. A component comprising:
    a femoral component of a knee prosthesis comprising:
        a bone-facing surface;
        an articulation surface, wherein the articulation surface has a curvature that is configured to mate with a mating articulation surface selected from at least one of a tibial surface, a patellar surface, a tibial component or a patellar component;

an anterior end of the articulation surface;

a posterior end of the articulation surface;

a claw extending (1) from an abrupt transition in a radius of the curvature, wherein the abrupt transition in the radius occurs in an anterior-posterior plane of at least one of the anterior most distal end of the articulation surface or the posterior most distal end of the articulation surface and (2) from an abrupt transition in a radius of the bone-facing surface, wherein the claw (1) is not configured to mate with the mating articulation surface, and (2) is configured to dig into tissue of a patient; and a rib element protruding from the bone-facing surface, wherein the rib element is elongated along a first axis, wherein the rib element comprises a free edge, and wherein the free edge of the rib element comprises a bulbous terminus along at least a portion of a length of the rib element.

* * * * *